United States Patent
Lachaine

(10) Patent No.: US 10,134,155 B2
(45) Date of Patent: Nov. 20, 2018

(54) SYSTEMS AND METHODS FOR REAL-TIME IMAGING

(71) Applicant: Elektra Limited, Montreal (CA)

(72) Inventor: Martin Emile Lachaine, Montreal (CA)

(73) Assignee: Elekta Limited, Montreal (CA)

( * ) Notice: Subject to any disclaimer, the term of this patent is extended or adjusted under 35 U.S.C. 154(b) by 69 days.

(21) Appl. No.: 15/357,193

(22) Filed: Nov. 21, 2016

(65) Prior Publication Data

US 2018/0144510 A1    May 24, 2018

(51) Int. Cl.
| G06T 11/00 | (2006.01) |
| A61B 6/03 | (2006.01) |
| A61B 6/00 | (2006.01) |
| G06T 7/00 | (2017.01) |

(52) U.S. Cl.
CPC ............ G06T 11/003 (2013.01); A61B 6/032 (2013.01); A61B 6/4085 (2013.01); A61B 6/5205 (2013.01); G06T 7/0012 (2013.01); G06T 2207/10081 (2013.01)

(58) Field of Classification Search
CPC ... G06T 7/0012; G06T 11/003; G06T 11/006; G06T 2207/10081; G06T 2211/40; A61B 6/03; A61B 6/032; A61B 6/5205
See application file for complete search history.

(56) References Cited

U.S. PATENT DOCUMENTS

| 5,461,651 | A | 10/1995 | Tam | 378/4 |
| 6,842,502 | B2 | 1/2005 | Jaffray et al. | 378/65 |
| 8,331,526 | B2 | 12/2012 | van Herk et al. | 378/4 |
| 8,358,738 | B2 | 1/2013 | Brown | 378/65 |
| 2004/0258194 | A1 | 12/2004 | Chen et al. | 378/4 |
| 2007/0010731 | A1 | 1/2007 | Mistretta | 600/407 |
| 2009/0123048 | A1* | 5/2009 | Leroux et al. | 382/131 |
| 2009/0232377 | A1 | 9/2009 | Miao et al. | 382/131 |
| 2010/0119033 | A1 | 5/2010 | Li et al. | 378/5 |
| 2011/0206178 | A1 | 8/2011 | van Herk et al. | 378/19 |

(Continued)

FOREIGN PATENT DOCUMENTS

WO    WO-2018090141 A1    5/2018

OTHER PUBLICATIONS

International Search Report and Written Opinion for corresponding Application No. PCT/CA2017/051373 dated Feb. 9, 2018 (14 pages).

(Continued)

*Primary Examiner* — Andrew W Johns
(74) *Attorney, Agent, or Firm* — Schwegman Lundberg & Woessner, P.A.; Sanjay Agrawal

(57) ABSTRACT

Embodiments of the present disclosure are directed to a system for generating three-dimensional images of a target region of a patient. The system may include at least one computer system. The computer system may be configured to receive a plurality of non-parallel projection images of the target region of the patient, convert the plurality of non-parallel projection images into a non-spatial domain, reconstruct a three-dimensional image from the plurality of non-parallel projection images in the non-spatial domain, and convert the reconstructed three-dimensional image from the non-spatial domain to the spatial domain.

67 Claims, 17 Drawing Sheets

(56) References Cited

U.S. PATENT DOCUMENTS

2012/0035462 A1    2/2012    Maurer et al. ............... 600/411
2014/0135615 A1    5/2014    Kruip .................. A61N 5/1039

OTHER PUBLICATIONS

Cai, J., et al., *Cine cone beam CT reconstruction using low-rank matrix factorization: algorithm and a proof-of-principle study.* IEE Transactions on Medical Imaging, 2014. 33(8): p. 1581-1591.

Li, R., et al., *3D tumor localization through real-time volumetric x-ray imaging for lung cancer radiotherapy.* Medical Physics, 2011. 38(5): p. 2783-2794.

Li, R., et al., *Real-time volumetric image reconstruction and 3D tumor localization based on a single x-ray projection image for lung cancer radiotherapy.* Medical Physics, 2010. 37(6): p. 2822-2826.

Xu, Y., et al., *A method for real-time volumetric imaging in radiotherapy using single x-ray projection.* arXiv preprint arXiv:1407.0667, 2014.

\* cited by examiner

SYSTEMS AND METHODS FOR REAL-TIME IMAGING

TECHNICAL FIELD

Aspects of the present disclosure relate generally to radiotherapy treatment systems, and, specifically, to methods and systems for real-time imaging and motion management for use with, e.g., radiotherapy treatment systems.

BACKGROUND

Radiation therapy (also referred to as radiotherapy) may be used in the treatment of cancer or other pathologies. Radiotherapy involves delivering a prescribed dose of radiation to a target region of a patient, for example, to a tumor or other cancerous tissue. The target region may be imaged prior to the administration of radiotherapy, and a treatment plan may be formulated based on, e.g., the size, location, and/or orientation of the target and the surrounding structures, among other things. A linear accelerator (linac) may then be used to deliver radiation to the target region of the patient. The linac may direct photons (e.g., an X-ray), electrons, or other subatomic particles toward a target, such as a tumor.

After initial images of the target are acquired, however, the location and/or orientation of the target region may change. For example, the patient may shift during transfer to the treatment room, during movement within the treatment room (e.g., positioning on a couch, bed, or table), or during the administration of radiotherapy. For example, a patient may move voluntarily or involuntarily due to regular biological processes, including, e.g., breathing, swallowing, blinking, twitching, peristalsis, digestion, beating of the heart, coughing, passing gas, or other movements.

Changes in the location and/or orientation of the target region may reduce the efficacy of radiotherapy. For example, if the actual orientation or location of the target region is different than the assumed orientation or location based on prior imaging, then the correct dose of radiation may not be delivered to the intended target region. Additionally, surrounding healthy structures may receive radiation instead of, or in addition to, the intended target region. Exposing the wrong area to radiation may ultimately harm or kill surrounding healthy cells. Accordingly, real-time, accurate, 3D localization and tracking of a target may be desirable during radiotherapy to account for movement (e.g., movement of a tumor or movement of surrounding healthy structures) as radiation is delivered to the patient.

Medical imaging may be used to control for and accommodate changes in the location and/or orientation of a target region after the acquisition of initial imaging. Imaging systems, including, for example, CT, cone-beam CT (CBCT), fluoroscopy, X-ray, and/or MRI may be used before and/or during the delivery of radiotherapy to determine the location of and track a target region. Such imaging systems may be incorporated into radiotherapy delivery systems, for example, into an image-guided linac, to enable gating or tracking strategies to compensate for movement of the target region in real time during the delivery of radiotherapy. Such technology may be referred to as image-guided radiation therapy (IGRT) or intensity modulated radiation therapy (IMRT).

Currently available technology, however, has struggled to produce accurate, real-time localization of a target region and/or surrounding structures. Conventional linear accelerators may include a kilovoltage (kV) imager affixed to a gantry, enabling imaging perpendicular to a megavoltage (MV) treatment beam. A kV imager may be used to acquire 2D X-ray projections at any given point in time as the imager moves around the patient on the gantry.

Although kV projection images alone are useful in some instances, particularly for high-contrast targets or patients with embedded fiducials, it is often desirable to acquire multiple projections from multiple viewpoints. For example, the X-ray imager may be rotated in an arc around the patient (e.g., along a gantry) to acquire new projection images at angular increments. A 3D image may then be reconstructed from multiple projections using principles of tomography.

Yet, the 3D images reconstructed using currently available technology generally are not able to accurately depict the location and orientation of a target area in real time. This is because as an imager moves along the gantry to capture images of the target region from different angles, only the current projection image is accurate—all of the previously acquired projection images may be stale and no longer depict the current location of the target region. While the stale images are needed to reconstruct a 3D image, the stale images may contain incorrect location data. Only the current projection indicates the true location and orientation of the target region at that time, thus averaging the current image with the stale images may decrease the accuracy of the resulting image. Attempts have been made to combine current and stale images using algorithms and interpolation, but many of these techniques have struggled with inaccuracies. The unique cone-beam shape of CBCT complicates the application of many algorithms, and performing these algorithms in the spatial domain has proved unwieldy because of the amount of data that must be computed so quickly. In some instances, the algorithms used have been too computationally complex for fast implementation on 3D data and thus are not useful for real-time motion management. The construction of real-time (3D+T) CBCT images has been referred to in the literature as 'cine CBCT'.

As an alternative solution to detecting real-time motion during treatment, attempts have been made to detect the target directly in each individual projection. The target may then be known to exist along a ray line connecting the detected image pixel and the target source. If stereoscopic kV imaging is used (e.g., Cyberknife technology), then the target position may be determined by intersecting ray lines from each detector. If a single kV detector is present, as is the case with many modern linacs, then monoscopic kV imaging techniques may be used to estimate the position of the target along the ray line. Yet, such techniques may result in the loss of information regarding the full target and surrounding tissues. They also rely on being able to detect the target in each kV projection, but kV imaging may generally only be effective for imaging high-contrast targets, for example, with the use of implanted fiducials, which limits the applicability of such techniques. Such attempts have been termed 'cine projection' solutions. With a 'cine CBCT' rather than a 'cine projection' solution, lower contrast targets may be detected, often without the need for fiducials, but again, the computational power necessary to perform such calculations may not be feasible for use with real-time applications.

Accordingly, a need exists for systems and methods that allow for the generation of accurate, real-time images of a target region that allow a healthcare provider to track the location and/or orientation of the target region in a patient before, during, and/or after the administration of radiotherapy. There also exists a need for systems and methods of tracking movement of lower contrast targets and for tracking movement of targets without using fiducials.

SUMMARY OF THE INVENTION

Embodiments of the present disclosure may be directed to a system for generating three-dimensional images of a target region of a patient. The system may include at least one computer system. The computer system may be configured to receive a plurality of non-parallel projection images of the target region of the patient, convert the plurality of non-parallel projection images into a non-spatial domain, reconstruct a three-dimensional image from the plurality of non-parallel projection images in the non-spatial domain, and convert the reconstructed three-dimensional image from the non-spatial domain to the spatial domain.

Various embodiments of the system may include one or more of the following features. The plurality of non-parallel projection images may be a plurality of cone-beam computed tomography projection images, or the plurality of non-parallel projection images may include one current projection image obtained at a first time period and a plurality of stale projection images obtained at one or more time periods before the first time period. In some aspects, the one current projection image may be used as a constraint to which the plurality of stale projection images may be fitted during reconstruction of the three-dimensional image in the non-spatial domain. The non-spatial domain may be a first non-spatial domain, and the at least one computer system may be further configured to convert the reconstructed three-dimensional image into a second non-spatial domain before converting the reconstructed three-dimensional image into the spatial domain. In some aspects, the first non-spatial domain may be d-space, and the second non-spatial domain may be k-space. The non-spatial domain may be a second non-spatial domain, and the at least one computer system may be further configured to convert the plurality of non-parallel projection images to a first non-spatial domain before converting the plurality of non-parallel projection images into the second non-spatial domain. The first non-spatial domain may be d-space, and the second non-spatial domain may be k-space.

In some aspects, the target region may include a tumor. In some variations, the system may further comprise a linear accelerator configured to acquire the plurality of non-parallel projection images and transmit them to the computer system. The at least one computer system may be further configured to modify a characteristic of the linear accelerator based on a location of a target within the target region in the reconstructed three-dimensional image. The characteristic of the linear accelerator may be a characteristic of a beam of radiation output from the linear accelerator, or the characteristic of the linear accelerator may be an orientation of at least a portion of the linear accelerator relative to the patient. The at least one computer system may further be configured to modify a treatment plan based on a location of a target within the target region in the reconstructed three-dimensional image.

In some variations of the disclosure, the at least one computer system may be further configured to receive one or more second non-parallel projection images of the target region of the patient, convert the one or more second non-parallel projection images into the non-spatial domain, reconstruct a second three-dimensional image from at least the one or more second non-parallel projection images in the non-spatial domain, and convert the reconstructed second three-dimensional image from the non-spatial domain to the spatial domain. In some variations, the system may be configured to receive, convert, reconstruct, and convert in real time.

Embodiments of the present disclosure may be drawn to a computer-implemented method for generating three-dimensional images of a target region of a patient. The method may include receiving a plurality of non-parallel projection images of the target region of the patient, converting the plurality of non-parallel projection images into a non-spatial domain, reconstructing a three-dimensional image from the plurality of non-parallel projection images in the non-spatial domain, and converting the reconstructed three-dimensional image from the non-spatial domain to the spatial domain.

Various embodiments of the method may include one or more of the following features. The plurality of non-parallel projection images may be a plurality of cone-beam computed tomography projection images, or the plurality of non-parallel projection images may include one current projection image obtained at a first time period and a plurality of stale projection images obtained at one or more time periods before the first time period. The one current projection image may be used as a constraint to which the plurality of stale projection images may be fitted when reconstructing the three-dimensional image in the non-spatial domain. In some aspects, the non-spatial domain may be a first non-spatial domain, and the method may further comprise converting the reconstructed three-dimensional image into a second non-spatial domain before converting the reconstructed three-dimensional image into the spatial domain. The first non-spatial domain may be d-space, and the second non-spatial domain may be k-space. In some aspects, the non-spatial domain may be a second non-spatial domain, and the method may further comprise converting the plurality of non-parallel projection images to a first non-spatial domain before converting the plurality of non-parallel projection images into the second non-spatial domain. The first non-spatial domain may be d-space, and the second non-spatial domain may be k-space.

In some variations of the disclosure, the target region may include a tumor, or the method may further comprise modifying a treatment plan to be delivered by a medical device based on a location of a target within the target region in the reconstructed three-dimensional image. The method may further comprise receiving one or more second non-parallel projection images of the target region of the patient, converting the one or more second plurality of non-parallel projection images into the non-spatial domain, reconstructing a second three-dimensional image from the one or more second non-parallel projection images in the non-spatial domain, and converting the reconstructed second three-dimensional image from the non-spatial domain to the spatial domain. Each of the receiving, converting, reconstructing, and converting may be performed in real time.

Embodiments of the present disclosure may also be drawn to a non-transitory computer-readable medium storing instructions that, when executed by a processor, cause the processor to perform a method of generating three-dimensional images of a target region of a patient. The method may include receiving a plurality of non-parallel projection images of the target region of the patient, converting the plurality of non-parallel projection images into a non-spatial domain, reconstructing a three-dimensional image from the plurality of non-parallel projection images in the non-spatial domain, and converting the reconstructed three-dimensional image from the non-spatial domain to the spatial domain.

Various embodiments of the method may include one or more of the following features. The plurality of non-parallel projection images may be a plurality of cone-beam computed tomography projection images, or the plurality of non-parallel projection images may include one current projection image obtained at a first time period and a plurality of stale projection images obtained at one or more time periods before the first time period. The one current projection image may be used as a constraint to which the plurality of stale projection images may be fitted when reconstructing the three-dimensional image in the non-spatial domain.

In some aspects, the non-spatial domain may be a first non-spatial domain, and the method may further comprise converting the reconstructed three-dimensional image into a second non-spatial domain before converting the reconstructed three-dimensional image into the spatial domain. The first non-spatial domain may be d-space, and the second non-spatial domain may be k-space. In some aspects, the non-spatial domain may be a second non-spatial domain, and the method may further comprise converting the plurality of non-parallel projection images to a first non-spatial domain before converting the plurality of non-parallel projection images into the second non-spatial domain. The first non-spatial domain may be d-space, and the second non-spatial domain may be k-space. The target region may include a tumor, or the method may further comprise modifying a treatment plan to be delivered by a medical device based on a location of a target within the target region in the reconstructed three-dimensional image.

Various aspects of the method may also include receiving one or more second non-parallel projection images of the target region of the patient, converting the one or more second non-parallel projection images into the non-spatial domain, reconstructing a second three-dimensional image from the one or more second non-parallel projection images in the non-spatial domain, and converting the reconstructed second three-dimensional image from the non-spatial domain to the spatial domain. In some aspects, each of the receiving, converting, reconstructing, and converting may be performed in real time.

Further embodiments of the present disclosure may also be drawn to a system for generating three-dimensional images of a target region of a patient comprising at least one computer system. The computer system may be configured to receive cone-beam computed tomography imaging data, convert the imaging data from a spatial domain into a first non-spatial domain, convert the imaging data from the first non-spatial domain into a second non-spatial domain, reconstruct a three-dimensional image from the imaging data in at least one of the first non-spatial domain and the second non-spatial domain, and convert the reconstructed three-dimensional image from the second non-spatial domain to the spatial domain.

Various aspects of the system may include one or more of the following features. The first non-spatial domain may be d-space, and the second non-spatial domain may be k-space. The imaging data may include a plurality of cone-beam computed tomography projections.

Further embodiments of the present disclosure may be drawn to a computer-implemented method for generating three-dimensional images of a target region of a patient. The method may include receiving cone-beam computed tomography imaging data, converting the imaging data from a spatial domain into a first non-spatial domain, converting the imaging data from the first non-spatial domain into a second non-spatial domain, reconstructing a three-dimensional image from the imaging data in at least one of the first non-spatial domain and the second non-spatial domain, and converting the reconstructed three-dimensional image from the second non-spatial domain to the spatial domain.

Various aspects of the method may include one or more of the following features. The first non-spatial domain may be d-space, and the second non-spatial domain may be k-space. The imaging data may include a plurality of cone-beam computed tomography projections.

Additional embodiments of the present disclosure may be drawn to a non-transitory computer-readable medium storing instructions that, when executed by a processor, cause the processor to perform a method of generating three-dimensional images of a target region of a patient. The method may include receiving cone-beam computed tomography imaging data, converting the imaging data from a spatial domain into a first non-spatial domain, converting the imaging data from the first non-spatial domain into a second non-spatial domain, reconstructing a three-dimensional image from the imaging data in at least one of the first non-spatial domain and the second non-spatial domain, and converting the reconstructed three-dimensional image from the second non-spatial domain to the spatial domain.

Various aspects of the method may also include one or more of the following features. The first non-spatial domain may be d-space, and the second non-spatial domain may be k-space. The imaging data may include a plurality of cone-beam computed tomography projections.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings:

FIGS. 3A to 3C schematically depict an exemplary mathematical process that may be performed on imaging data, e.g., medical imaging data, in accordance with various embodiments of the present disclosure.

DETAILED DESCRIPTION

Reference will now be made in detail to the exemplary embodiments of the present disclosure described below and illustrated in the accompanying drawings. Wherever possible, the same reference numbers will be used throughout the drawings to refer to same or like parts. The term "exemplary" is used in the sense of "example," rather than "ideal." As used herein, the term "real time" means that data is processed at a speed that allows output or feedback to be made available during the course of a radiotherapy session. In some embodiments, this may mean that data is processed and a 3D image is generated within, e.g., 300 milliseconds, within 500 milliseconds, within 2 seconds, within 30 seconds, or within several minutes. In some embodiments, the speed of data processing may depend, at least in part, on the location of the target region being treated. For example, for a target that may be affected by respiratory motion (e.g., in the thorax or abdomen) or by cardiac motion, faster data processing may be used than for a slower-moving target region, e.g., the prostate. In some embodiments, image data may be processed prior to the completion of a subsequent projection or prior to the completion of a certain number of projections. Although many of the exemplary embodiments of the present disclosure refer to CBCT and conventional linac systems, it will be understood by those of ordinary skill in the art that the disclosed embodiments may be used in combination with any suitable imaging modality and for any suitable type of radiotherapy system. For example, embodiments of the disclosure may be used in conjunction with MRI-linac systems, Gamma Knife systems, or other suitable radiation delivery and imaging modalities.

As discussed above, real-time imaging of a target region of a patient has proven elusive, leaving a need for accurate and timely tracking of a target region's movement during radiation therapy. Aspects of the disclosure are related to integrated imaging linac systems and imaging methods that use a current projection image as a constraint indicative of the 'true' real-time location of the target. Stale projection images then may be used to fill in the remaining information and reconstruct 3D or 4D images, with the current image acting as the constraint. The reconstruction may occur according to a number of various methods, as will be described further below. As new projection images are sequentially taken, new current images may be used as constraints and new 3D reconstructions may be generated in real time. Accordingly, aspects of the disclosure may allow for generation of 3D images that evolve in real time to depict the true, current location and/or orientation of the target region. Being able to generate real-time images may thus allow healthcare providers to track motion of the target region before, during, or after treatment, and may allow providers to modify and/or stop the treatment in response to movement of the target region, if needed.

Figure 1A:
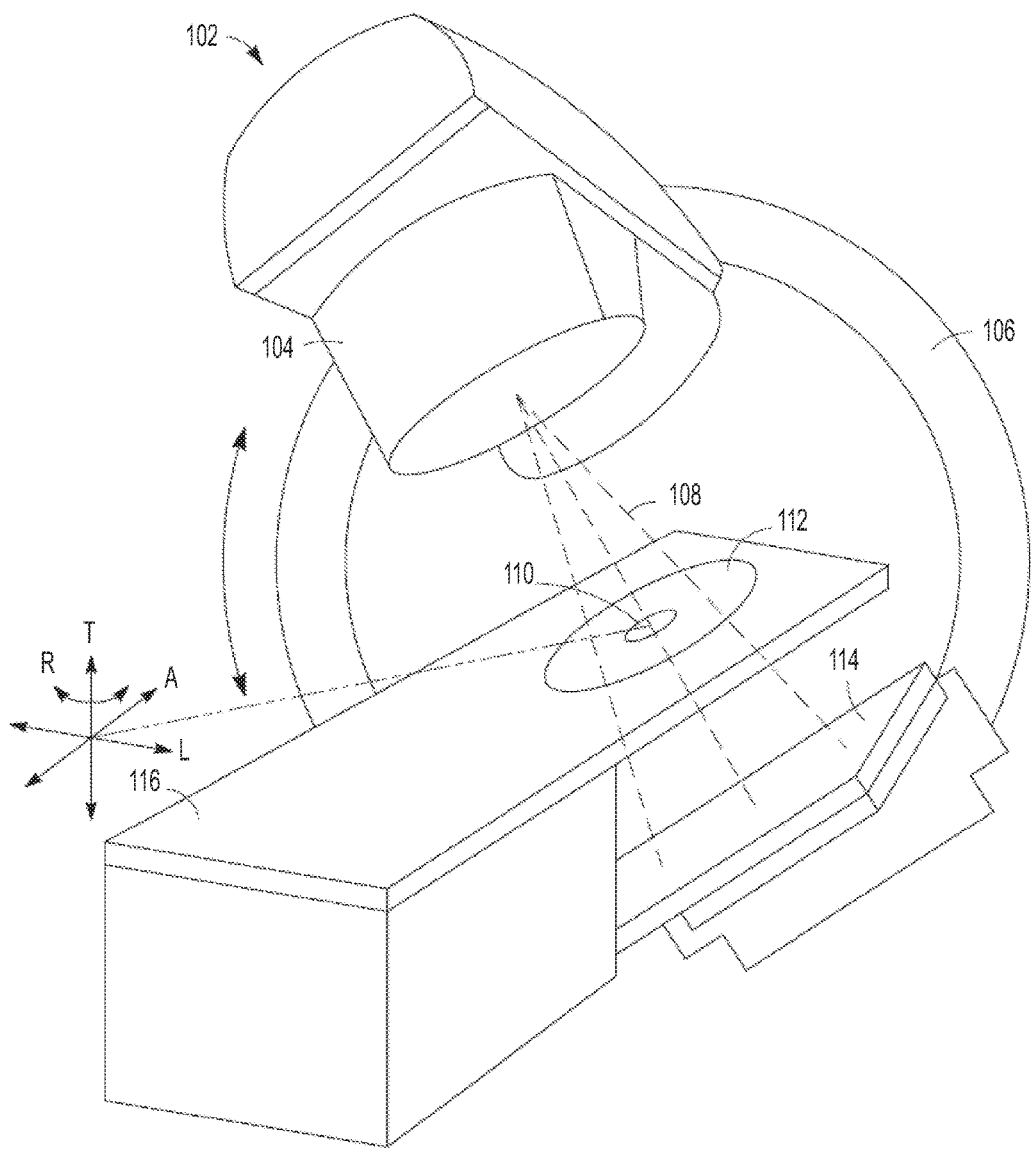
FIG. 1A depicts an exemplary radiotherapy device that may be used to implement various embodiments of the present disclosure.

FIG. 1A depicts an exemplary radiation therapy system 102 in the form of a linac. Radiation therapy system 102 may be part of a larger imaging and radiotherapy system 100, shown in FIG. 1C. Radiation therapy system 102 and/or imaging and radiotherapy system 100 (shown in FIG. 1C) may be used to provide real-time image guidance in accordance with various aspects of the disclosure. The systems may use images obtained in real time to track motion of a target region and/or to control or adapt a radiation therapy treatment plan in real time, as described further below.

System 102 may include a radiation therapy output 104 configured to deliver a beam of radiation 108 to a portion of a patient located in region 112. Radiation therapy output 104 may include one or more attenuators or collimators, such as a multi-leaf collimator (MLC). Attenuators and/or collimators may be used to shape beam of radiation 108, e.g., based on the size and/or shape of the target region.

System 102 may also include a surface 116, for example, a table, bed, or couch, and a patient or a portion of a patient may be positioned on region 112 of surface 116 to receive a prescribed radiation therapy dose according to a radiation therapy treatment plan. In some embodiments, surface 116 may move relative to system 102. For example, surface 116 may move in a transverse (T) direction, a lateral direction (L), an axial direction (A), and/or may rotate about a transverse axis (R), e.g., to assist with moving the patient into and out of system 102, positioning the patient within system 102, setting up system 102, and/or cleaning or repairing system 102.

Radiation therapy output 104 may be coupled to a gantry 106 or other mechanical support and may be configured to move relative to the patient, relative to system 102, and/or relative to gantry 106. For example, radiation therapy output 104 may rotate on gantry 106 around an axis (A) extending through a central region of gantry 106. Radiation therapy output 104 may additionally or alternatively be moveable in a transverse direction or a lateral direction. This may, e.g., allow radiation therapy output 104 to be positioned relative to the patient.

The coordinate system (including axes A, T, and L) shown in FIG. 1A may have an origin located at an isocenter 110. Isocenter 110 may be defined as the location where radiation therapy beam 108 intersects the origin of the coordinate axis to deliver a prescribed radiation dose to a location on or within a patient. For example, isocenter 110 may be defined as a location where radiation therapy beam 108 intersects the patient when emitted from various rotational positions as radiation therapy output 104 rotates around axis A along gantry 106.

In an exemplary embodiment, a detector 114 may be located within a field of radiation therapy beam 108. Detector 114 may include a flat panel detector, e.g., a direct detector or a scintillation-based detector. Detector 114 may be mounted on gantry 106 generally opposite radiation therapy output 104 and may rotate with radiation therapy output 104 to maintain alignment with therapy beam 108 as gantry 106 rotates. In this manner, detector 114 may be used to monitor radiation therapy beam 108, and/or detector 114 may be used for imaging, such as, for example, portal imaging of a projection of radiation therapy beam 108 through region 112. Region 112 may define a plane, and a projection of radiation therapy beam 108 in region 112 may be referred to as a "Beam Eye View" of region 112.

One or more of surface 116, radiation therapy output 104, and/or gantry 106 may be manually or automatically positioned relative to one another in system 102, and characteristics of radiation therapy beam 108 output by radiation therapy output 104 may be determined according to a specified dose of radiation intended for the patient for a particular radiotherapy delivery instance during a treatment. A sequence of radiation therapy deliveries may be specified according to a radiation therapy treatment plan, for example, one or more different orientations or locations of gantry 106, surface 116, and/or radiation therapy output 104 may be adjusted based on the sequence. For example, radiation therapy output 104 may move along gantry 106 around axis A and may output a radiation therapy beam 108 at a number of different locations. Thus, a projection of radiation from radiation therapy output 104 may be directed at the target region from a number of different directions. In some embodiments, deliveries of radiation therapy from different angles may occur sequentially but each may intersect at isocenter 110. In this way, a prescribed cumulative dose of radiation therapy may thereby be delivered to a target region within the patient. During delivery, exposure and damage to structures surrounding the target region may be reduced or avoided with precise delivery of radiation.

Radiation therapy system 102 may operate independently or may operate in conjunction with an imaging acquisition system, for example, an MR imaging, X-ray imaging, CT imaging, CBCT imaging, or any other suitable imaging acquisition system. Imaging by one or more components of an imaging system may acquire images before, during, and/or after radiotherapy treatment.

Figure 1B:
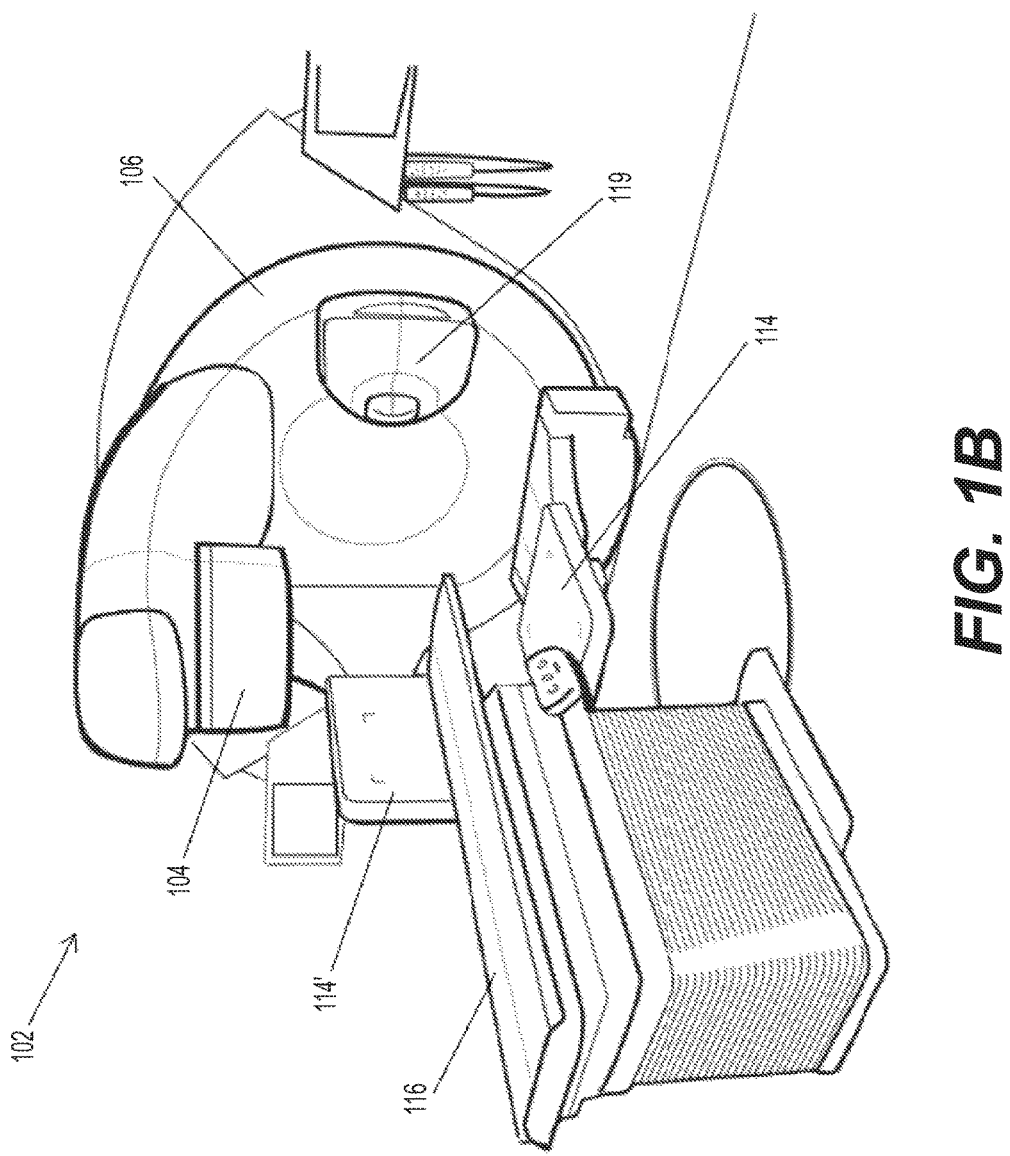
FIG. 1B depicts an exemplary radiotherapy device that may be used to implement various embodiments of the present disclosure.
Figure 1C:
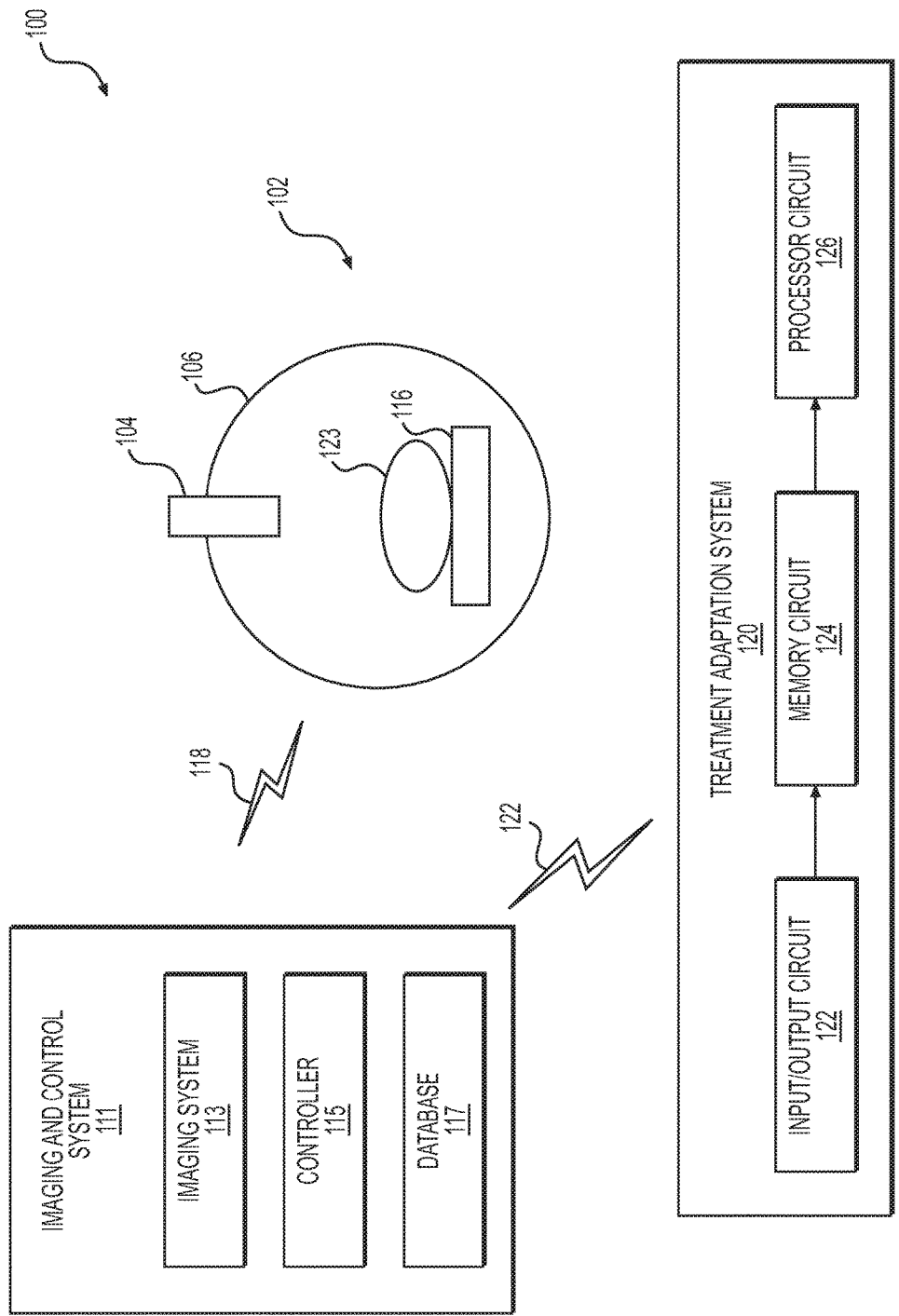
FIG. 1C depicts an exemplary system that may be used to provide real-time imaging in accordance with various embodiments of the present disclosure.

FIG. 1B depicts another exemplary radiation therapy system 102 that may be used alone or may be part of a larger imaging and radiotherapy system 100, like that shown in FIG. 1C. Radiation therapy system 102 of FIG. 1B may operate in a similar manner to radiation therapy system 102 of FIG. 1A. For example, the system of FIG. 1B may include a surface 116 for positioning a patient as well as a gantry 106, a radiation therapy output 104, and a detector 114 configured to rotate around the patient.

In addition to the components of FIG. 1A, however, radiation therapy system 102 of FIG. 1B includes an integrated kilovoltage (kV) source 119 and a corresponding detector 114' affixed to gantry 106. The radiation therapy system 102 of FIG. 1B may be referred to as a linac with on-board imaging. The kV source 119 and detector 114' may be offset by 90 degrees relative to radiation therapy output 104 and its corresponding detector 114, discussed above. This arrangement enables imaging perpendicular to beam of radiation 108 output by radiation therapy output 104, which, in some embodiments, may be a megavoltage (MV) treatment beam. The kV source 119 may be used to acquire 2D X-ray projections as kV source 119 moves around the patient along gantry 106.

The kV source 119 may include an x-ray tube and may be configured to deliver a beam of x-ray radiation to a target region within a patient. After passing through the patient, the beam of x-ray radiation may then strike corresponding detector 114'. Detector 114', like detector 114, may include a flat panel detector, e.g., a direct detector or a scintillation-based detector. Detector 114' may be mounted on gantry 106 generally opposite kV source 119 and may rotate with kV source 119 to maintain alignment with the beam output by kV source 119 as gantry 106 rotates. In this manner, detector 114' may be used for imaging.

In operation, a beam of radiation output by kV source 119 may also pass through isocenter 110 (described above in reference to FIG. 1A) as kV source 119 and corresponding detector 114' rotate along gantry 106. In some aspects, imaging captured with kV source 119 and detector 114' may provide better contrast than imaging provided using radiotherapy output 104 (e.g., MV imaging) and detector 114. Imaging may be acquired using kV source 119 and detector 114' instead of, or in addition to, imaging acquired using radiation therapy output 104 and detector 114. Aside from the inclusion of on-board kV source 119 and corresponding detector 114', radiation therapy system 102 of FIG. 1B may operate substantially similar to radiation therapy system 102 of FIG. 1A.

FIG. 1C depicts an exemplary imaging and radiotherapy system 100 that may be used to provide real-time imaging in accordance with various embodiments of the disclosure. Imaging and radiotherapy system 100 may use images obtained in real time to track, control, and/or adapt a radiation therapy treatment plan during the administration of radiotherapy. Imaging and radiotherapy system 100 may include a radiotherapy system 102 (e.g., a linac) of either FIG. 1A or FIG. 1B (collectively referred to as radiotherapy system 102). Imaging and radiotherapy system 100 may also include an imaging and control system 111, which may include an imaging system 113. In some embodiments, radiotherapy system 102 may incorporate all of the required imaging (e.g., radiotherapy system 102 may incorporate X-ray imaging or may incorporate MRI), while in some embodiments, a separate imaging system 113 may also be included in imaging and radiotherapy system 100 instead of, or in addition to, imaging integrated into the linac. Imaging system 113 may include, e.g., a CT or MRI machine that may be used in combination with system 102 to provide imaging before radiotherapy (e.g., during pre-treatment or pre-planning), during radiotherapy, or after radiotherapy. One or more other imaging systems may be additionally or alternatively included in or used with system 100 or imaging system 113, e.g., CT, CBCT, MRI, X-ray, positron emission tomography (PET), single-photo emission computed tomography (SPECT), ultrasound, or any other suitable medical imaging system. In some embodiments, all imaging may be fully integrated within system 102, no imaging system 113 may be included, and system 111 may simply be a control system.

Imaging and radiotherapy system 100 may further include a controller 115 in communication with system 102, as depicted by lightning bolt 118 (lightning bolt 118 may represent a wired or wireless connection). Imaging and control system 111 may also include a database 117, for example, to store acquired images. Imaging information received from imaging system 113 may be used to control and/or adapt treatment of a patient 123. Additionally or alternatively, imaging information received from an imaging system integrated within radiotherapy system 102 may be communicated to controller 115 and database 117 to adapt treatment of patient 123.

Imaging system 113 (or integrated imaging within radiotherapy system 102) may acquire images of a patient located within radiotherapy system 102. For example, during a treatment planning phase, a healthcare worker, e.g., physician, nurse, physicist, or technician, may use system 100 to acquire 3D planning image data prior to treatment of the patient, e.g., via the imaging system 113 or an integrated imaging system within radiotherapy system 102. The 3D planning image data may be used to determine a precise location of a target region of the patient, e.g., a tumor. In some embodiments, this planning image may be received in database 117 and/or memory circuit 124. As another example, immediately prior to treatment, e.g., several hours, days, or weeks after the 3D planning image was acquired, the healthcare worker may use system 100 or system 102 to acquire a new 3D image that may be used during the administration of radiotherapy. In embodiments of the present disclosure, imaging system 113 or an integrated imaging system within radiotherapy system 102 may acquire a plurality of images of at least a portion of the target region during a treatment session.

Controller 115 may control one or more aspects of system 100. For example, controller 115 may control portions of radiotherapy system 102. Controller 115 may control the position of the patient (e.g., by controlling movement of surface 116), may control the radiation dosage emitted from radiation therapy output 104, may control or adapt a beam aperture shape or size (e.g., to track the target region), and/or may control the movement and/or positioning of radiation therapy output 104 relative to patient 123 (e.g., by controlling rotation around gantry 106). In some embodiments, a common controller 115 may control both radiotherapy system 102 and imaging system 113. In some embodiments, there may be separate controllers for imaging system 113 and radiotherapy system 102, although the separate controllers may communicate with one another.

System 100 may include a treatment adaptation system (TAS) 120 in communication with imaging and control system 111, as represented by lightning bolt 122 (which may be a wired or wireless connection). TAS 120 may receive a previously obtained image, e.g., from a CT, CBCT, or MRI scan, that corresponds to an image acquired by imaging system 113 and/or by radiotherapy system 102. TAS 120 may include an input/output circuit 122 for receiving and transmitting data, a memory circuit 124 for buffering and/or storing data, and a processor circuit 126. Memory circuit 124, which may be any suitably organized data storage facility, may receive image data from imaging and control system 111. Memory circuit 124 may receive the image data via a wireless or wired connection or through conventional data ports and may include circuitry for receiving analog image data and analog-to-digital conversion circuitry for digitizing the image data. Memory circuit 124 may provide the image data to processor circuit 126, which may implement the functionality of the present invention in hardware or software, or a combination of both, on a general- or special-purpose computer. In some embodiments, processor circuit 126 may be a graphical processing unit (GPU).

During operation, radiotherapy system 102 may deliver radiation to a target region of a patient. Projection imaging information may be obtained using imaging incorporated within radiotherapy system 102 and/or imaging system 113. The imaging information collected may be stored in database 117, where other, prior imaging information may also be stored (for example, different types of imaging (e.g., CT, MRI, etc.), imaging from earlier in the treatment, imaging from pre-planning, or pre-treatment), and this imaging information may be raw or processed. Imaging information may be communicated from imaging and control system 111 to TAS via input/output circuit 122. The imaging information may be stored in memory circuit 124 and communicated to processor circuit 126. Processor circuit 126 may be programmed to carry out a number of different processes and may have software loaded on it to perform different processes, including the image reconstruction processes described further in the embodiments of this disclosure. The processed imaging information may be stored in memory circuit 124 and/or may be communicated to imaging and control system 111.

Memory circuit 124 may also store information regarding a treatment plan for patient 123, and this information may also be shared with processor circuit 126. Processor circuit 126 may compare real-time, processed imaging information from radiotherapy system 102 and/or imaging system 113 with the predetermined treatment plan for the patient to determine whether the radiotherapy being delivered to patient 123 matches the intended treatment plan for that radiotherapy session. If a variation is detected between the actual delivery of radiotherapy (determined using the imaging information) and the treatment plan, and that variation falls outside of an allowable threshold of variation, then TAS 120 may communicate this to imaging and control system 111. TAS 120 may modify the treatment plan or may stop the radiotherapy treatment altogether, for example, if the variation is beyond a threshold level. This modification or cessation may be communicated to controller 115 of imaging and control system 111, which may control a portion of radiotherapy system 102. For example, controller 115 may alter a position of patient 123 via movement of surface 116, may alter the beam of radiation output from radiation therapy output 104, and/or may alter the location of radiation therapy output 104 via gantry 106. In this way, imaging information may be processed in real time and may be used to control the administration of radiotherapy in real time.

It should be noted that although a separate imaging and control system 111 and a separate TAS 120 are depicted, the systems may be combined into one unit or may be distributed in any suitable manner across multiple separate units. Additionally, one or more units may be located within the treatment administration area or may be located remote from the treatment area. In some embodiments, the processing and data analysis may be integrated into radiotherapy system 102, may be performed within larger imaging and radiotherapy system 100, or either system 100 or system 102 may be connected to a network that is connected to the Internet, and a computer remote from radiotherapy system 102 may perform the processing and analyses described below in embodiments of the present disclosure.

As described in more detail below and in accordance with this disclosure, TAS 120 may track the location and/or orientation of a target region in real time using a current imaging projection as a constraint to construct 3D images. Particularly, embodiments may accurately track the location and/or orientation of a target region in real time using CBCT imaging.

CBCT Imaging, d-Space, and Real-Time Analysis

With CBCT imaging, an X-ray source and a detector are fixed opposite one another on a rotating gantry. A patient is oriented on a surface within the linac system, and a divergent cone-shaped or pyramidal-shaped beam of ionizing radiation is directed from the source, through a target area of the patient, and to the detector. As the source and detector rotate around the patient along the arc of the gantry, multiple, sequential projection images of the target area are acquired along the arc of the gantry. For example, dozens of projections, hundreds of projections, or thousands of projections may be taken as the source and detector rotate around the patient along the gantry.

Figure 2:
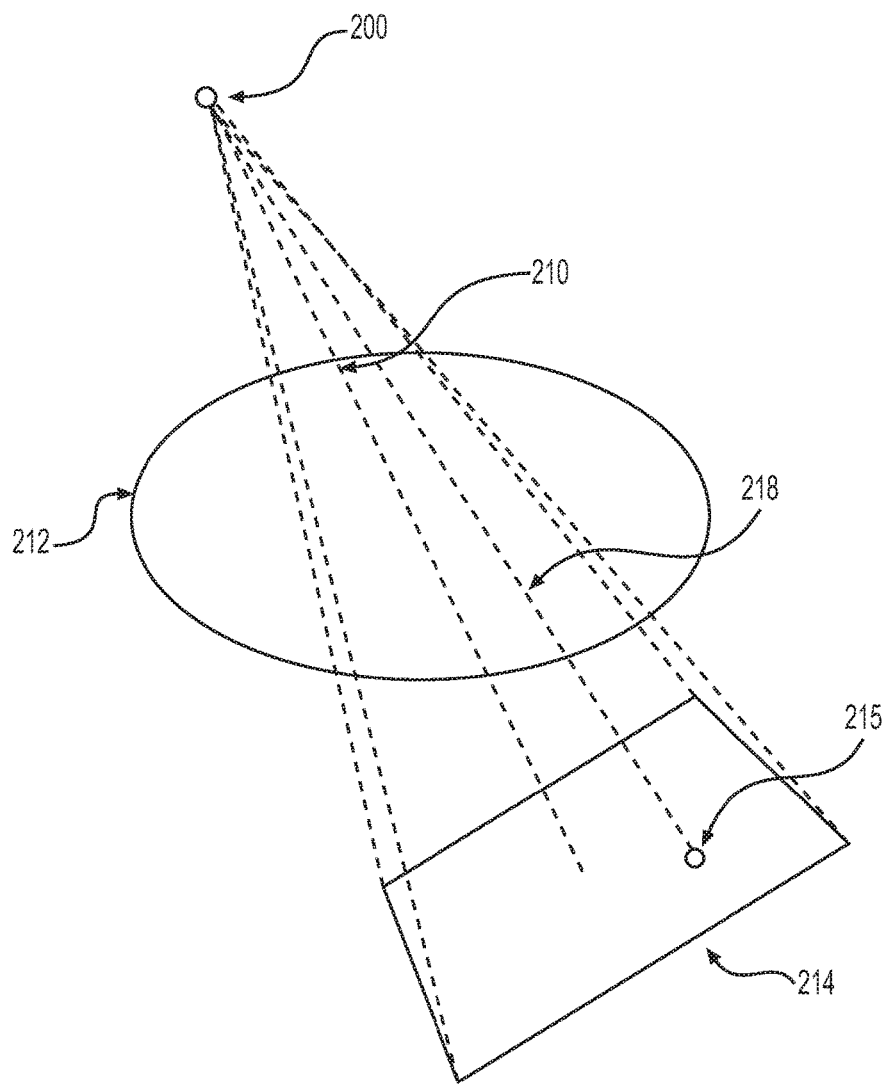
FIG. 2 schematically depicts an exemplary cone-beam projection for use with embodiments of the present disclosure.

Modern conventional linear accelerators generally include a kV imager affixed to a gantry, as depicted in FIG. 1B, enabling imaging perpendicular to an MV treatment beam. The geometry of kV imaging is often referred to as a cone-beam geometry, because ray lines 218 of radiation diverge out from a common source point 200 (e.g., out of kV source 119, or out of radiation therapy output 104), flaring out from a central axis 210 of the projection, as shown in FIG. 2. The divergent rays of radiation may strike a flat-panel detector 214 positioned opposite source point 200. A portion of a patient 212, for example, a target region of a patient, may be positioned between source point 200 and detector 214 so that ray lines 218 strike patient 212 at the target region.

A kV imager may acquire 2D x-ray projections sequentially at various points in time, but it is not possible to acquire the complete set of information needed to fully reconstruct a 3D image with a single projection. Using various degrees of approximation, however, full 3D images may be reconstructed from multiple CBCT projections. Yet, as discussed above, techniques developed up until this point have relied on approximations in reconstruction that introduce errors into the resulting images, making it difficult to accurately track the location and/or orientation of a target area in real time. Additionally, the amount of data that must be handled during such computations has slowed such calculations and has rendered them useless for use in real-time applications. As a result, because of the geometry of CBCT projections and because multiple CBCT projections from various angles are needed to reconstruct a 3D image of a target region, localization of the target region in real time has proved elusive. While CBCT imaging may work well clinically for imaging many anatomies, anatomies more affected by movement may be deleteriously affected by artifacts, blur, and location inaccuracies.

To reduce computational complexity, image reconstruction may be accomplished in k-space rather than in the spatial domain. K-space is the 3D space defined by the spatial frequencies in each Cartesian direction, $k_x$, $k_y$, and $k_z$. An image may be represented in k-space, for example, by calculating the 3D Fourier transform. This transformation compresses the image data, making it easier to conduct mathematical processes. Once transformed into k-space, the image may be reconstructed in k-space. Then, the reconstructed k-space image may be converted back into a 3D image in the spatial domain by taking the inverse Fourier transform of the reconstructed k-space image. In this way, computations may be performed with compressed data in k-space rather than larger amounts of uncompressed data in the spatial domain.

Figure 3C:
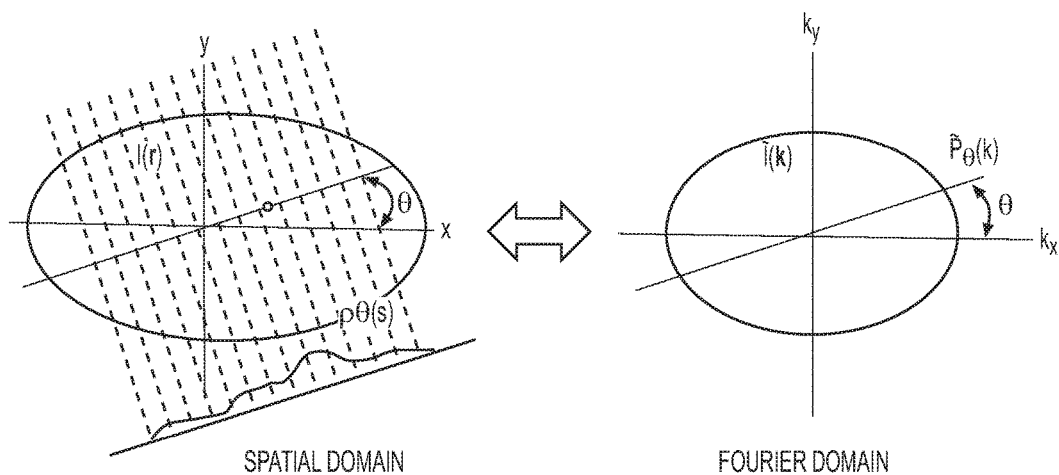
Figure 3C:
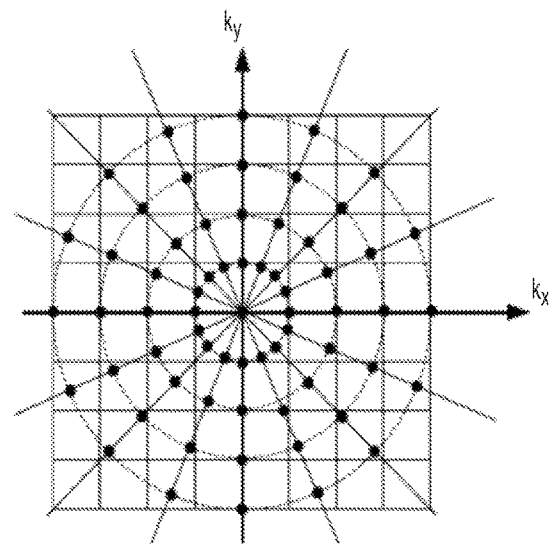

The concept of k-space is often discussed in terms of CT reconstruction with parallel-beam geometry. Reconstruction in k-space relies on use of the projection-slice theorem, which states that the Fourier transform of a projection in physical space is the same as a line in k-space. Referring to FIGS. 3A and 3B, if a projection at angle θ is taken that measures $p_θ(s)$ (FIG. 3A), then the Fourier transform is taken to obtain $\tilde{P}_θ(k)$ (FIG. 3B), the latter directly gives the points along a radial line in k-space at angle θ. By acquiring multiple projections at different angles θ, the points along multiple different radial lines in k-space can be known, and k-space can be filled, as shown in FIG. 3C, to construct the image in k-space $\tilde{I}(k)$. The Fourier transform of the k-space image can then be calculated to provide the image in the spatial domain, $I(r)$.

While Fourier reconstruction for parallel beam CT is a well-known concept, it is not commonly used in practice, because the points in k-space do not fall on a Cartesian grid. As a result, interpolation is required, which may cause artifacts in the resulting image. Recent work in the field of non-uniform fast Fourier transform (NUFFT) has made Fourier reconstruction more practical, but the projection-slice theorem still only works mathematically for parallel rays, and thus it has not been applied to CBCT, which utilizes diverging rays. Thus, direct extension of Fourier reconstruction to CBCT geometry is not possible. Accordingly, work with CBCT projections up to now has focused on the manipulation and reconstruction of CBCT projections in the spatial domain, which has proven complex and too unwieldy for real-time motion monitoring.

In embodiments of the disclosure, a new concept has been developed that moves away from reliance on a 2D projection consisting of multiple ray lines as the fundamental building block of image reconstruction and instead looks at a projection as a 1D projection along a single ray line. Embodiments of the disclosure reconstruct 3D images, including CBCT projection images, in the non-spatial domain. For example, ray line L in FIG. 4 originates at source 300, passes through patient 312, and strikes detector 314. A vector d connects an isocenter 322 with the closest point along ray line L and is perpendicular to ray line L. The 1D projection along ray line L is represented by $p_L$.

Figure 5A:
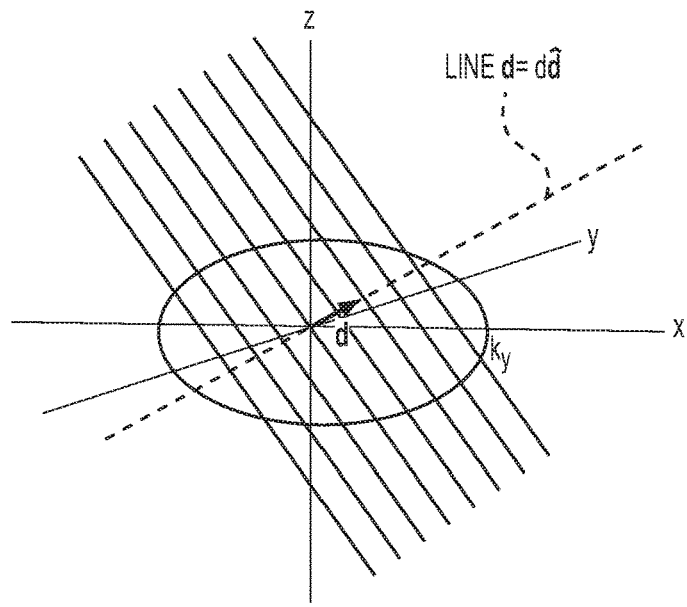
FIGS. 5A and 5B schematically depict an exemplary mathematical process that may be performed on imaging data in accordance with various embodiments of the present disclosure.
Figure 5B:
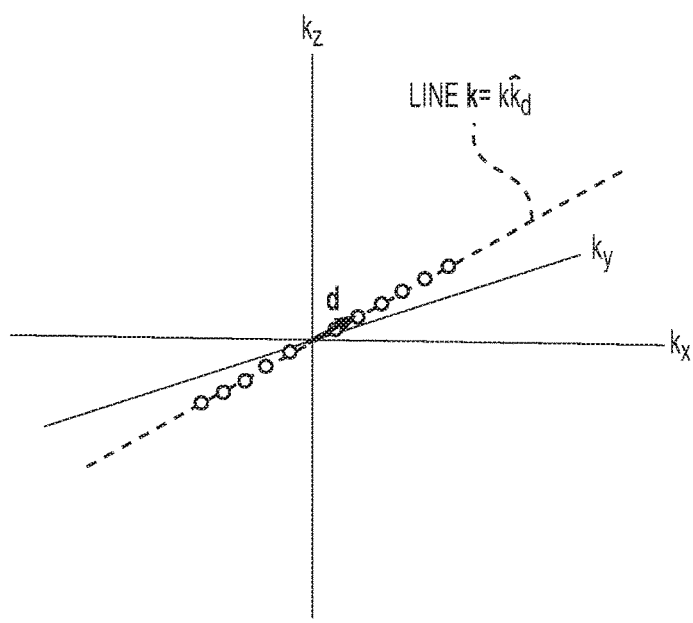

Going back to the traditional Fourier transform with parallel rays, if there were a collection of ray lines in the same direction as d, i.e., $d=d\hat{d}$, as shown in FIG. 5A, where $\hat{d}$ is a unit vector and d is the magnitude that varies from $-\infty$ to $\infty$, then there would be a function $p_L(d)$. Taking the Fourier transform would generate $\tilde{p}_L(k)$, depicted in FIG. 5B, which would fall along a radial line in k-space pointing in the same direction as $\hat{d}$, but which would be referred to as $\hat{k}_d$, because it would lie in k-space rather than the spatial domain.

Figure 4:
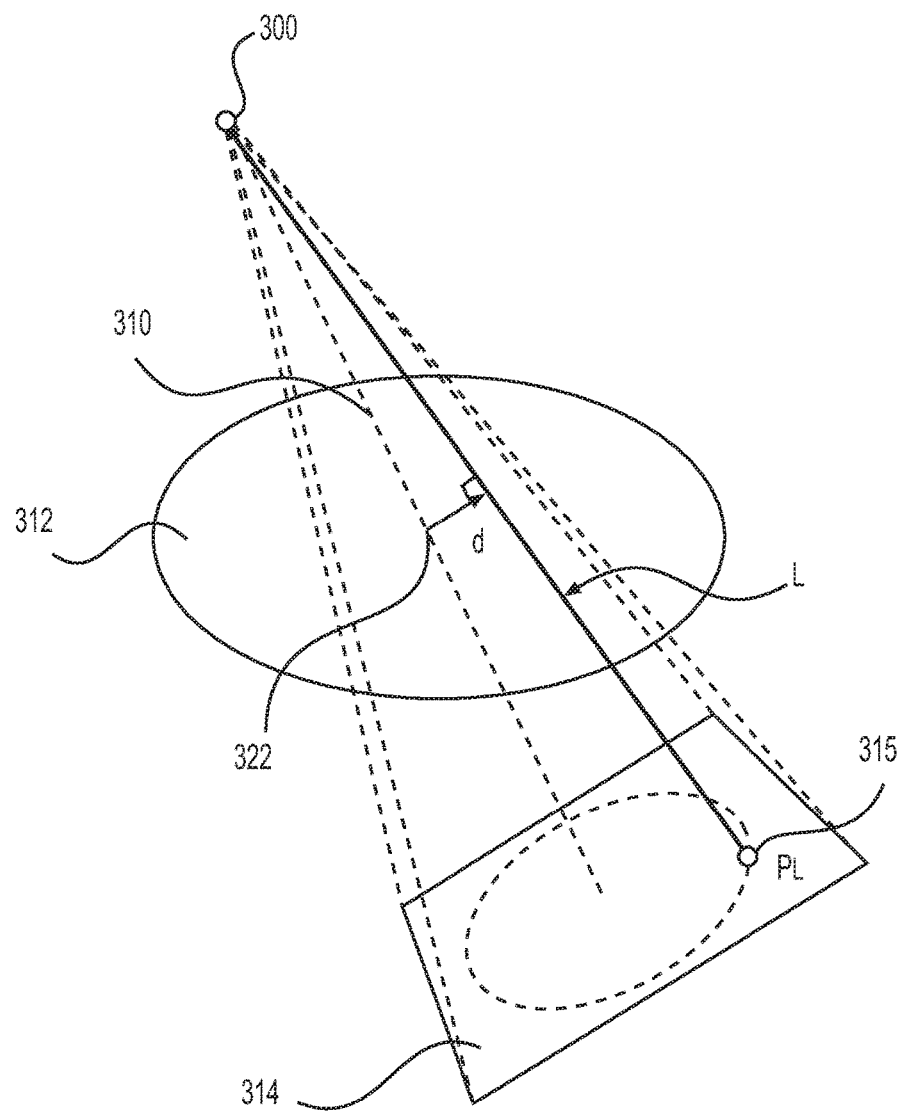
FIG. 4 schematically depicts an exemplary cone-beam projection for use with embodiments of the present disclosure.

Yet, in the divergent CBCT beam geometry of FIG. 4, there is no collection of parallel ray lines, so Fourier transform cannot be performed to convert the projection information into k-space. Accordingly, embodiments of the disclosure instead use vector d of FIG. 4 as a unique label for each projection line to transform imaging data into a non-spatial domain. The exemplary process is demonstrated visually in FIGS. 6A-6C.

Figure 6A:
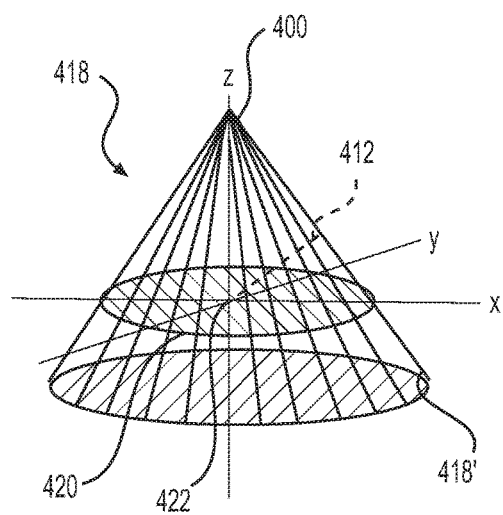
FIGS. 6A-6C schematically depict an exemplary mathematical process that may be performed on imaging data in accordance with various embodiments of the present disclosure.
Figure 6B:
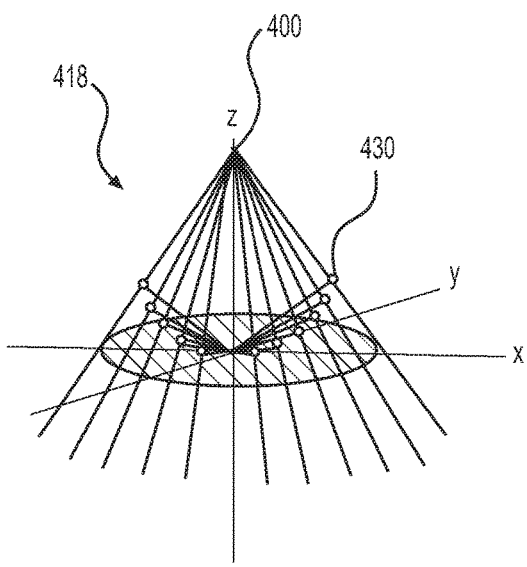
Figure 6C:
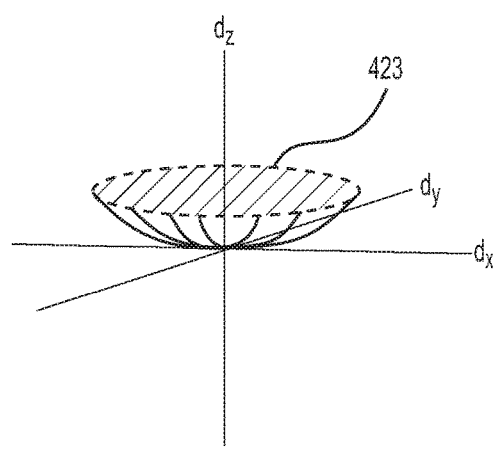

FIG. 6A depicts a single cone-beam projection formed of divergent ray lines 418 originating from source a 400. The divergent ray lines 418 are directed towards a target region 420 having an isocenter 422. The z-, x-, and y-axes have an origin that aligns with isocenter 422. A line 412 may be drawn from isocenter 422 to the closest point on ray line 418', perpendicular to ray line 418'. Accordingly, for ray line 418', line 412 acts like vector d from FIG. 4 and serves as a unique label ray line 418'. A vector d may be drawn for each ray line 418, extending from isocenter 422 to the closest point on each ray line 418, perpendicular to the respective ray line, providing each ray line with a unique label. Accordingly, the value of a discrete point along each divergent ray line 418 may be known. FIG. 6B depicts a vector d drawn from isocenter 422 to the closest point on each divergent ray line 418. The closest points to isocenter 422 on each ray line 418 are collectively labelled points 430. Each point 430 represents a known point along a respective ray line. For ease of visualization, points 430 in FIG. 6B are shown as flat, although in reality, points 430 would form a 3D bowl shape intersecting the divergent ray lines 418 of the cone beam. In this way, discrete points along divergent ray lines may be known and transformed into d-space, as opposed to k-space, as a new intermediate space in which calculations may be performed to generate real-time images for divergent rays. As defined herein, d-space is a Cartesian plane with axes $d=(d_x, d_y, d_z)$, shown in FIG. 6C. A given cone-beam projection with divergent ray lines 418 fills in d-space with known points 430, forming a curved plane of data resembling a bowl, as depicted by the collective points 430 in FIG. 6B and in FIG. 6C.

Figure 7A:
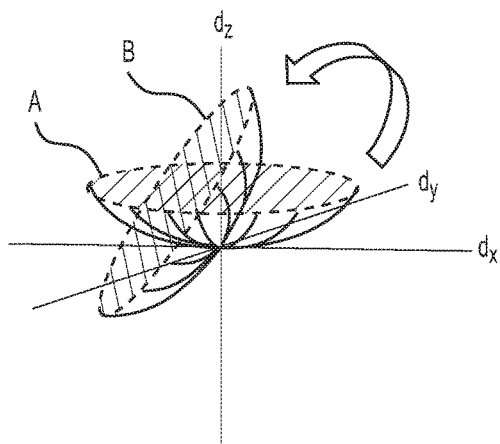
FIGS. 7A-7C schematically depict an exemplary mathematical process that may be performed on imaging data in accordance with various embodiments of the present disclosure.
Figure 7B:
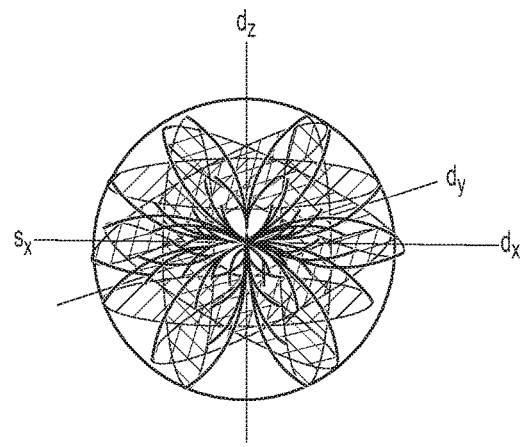

As the CBCT imager and source 400 rotate along the arc of the gantry, the cone-beam projections may rotate around the y-axis, and with it, the bowl generated by transforming the projections into d-space may also rotate around the $d_y$ axis. As a result, rotation of the projections around the y-axis may progressively fill in d-space with values that fall along the rotation path of the generated bowls in d-space, as shown in FIGS. 7A and 7B. FIG. 7A depicts a first set of points in d-space filled in by a projection at a position 'A' and then a second set of points in d-space filled in by a projection at a position 'B'. FIG. 7B depicts sets of points in d-space filled in by a plurality of projections from a single, complete rotation around the y-axis.

Figure 7C:
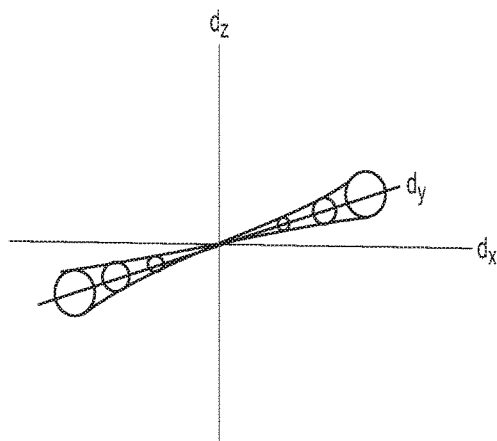

After a complete rotation, d-space may be filled in with the exception of 'trumpet-like' portions centered about the $d_y$ axis where the bowl did not touch the $d_y$ axis as it rotated around the $d_y$ axis, due to its curved shape. These trumpet-like portions are depicted in FIG. 7C. The trumpet regions shrink to zero as the cone beam becomes a parallel beam.

Figure 8A:
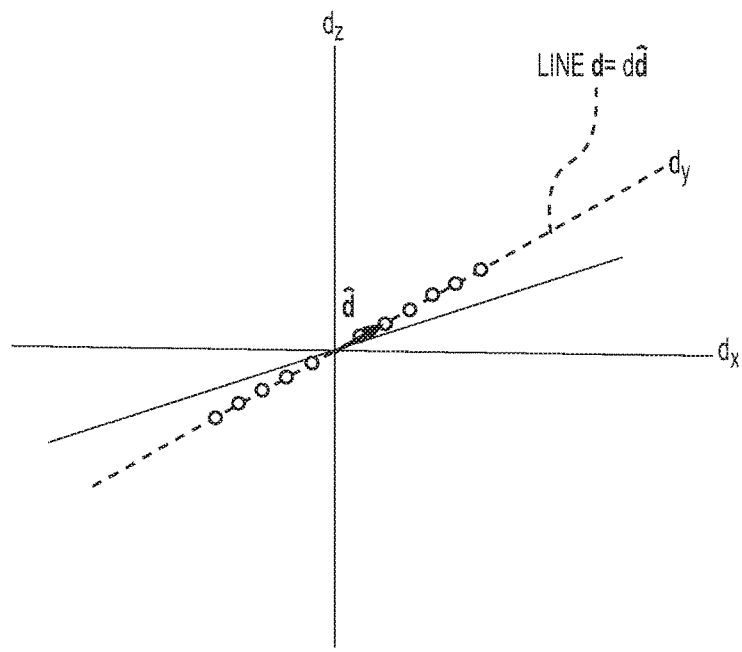
FIGS. 8A and 8B schematically depict an exemplary mathematical process that may be performed on imaging data in accordance with various embodiments of the present disclosure.
Figure 8B:
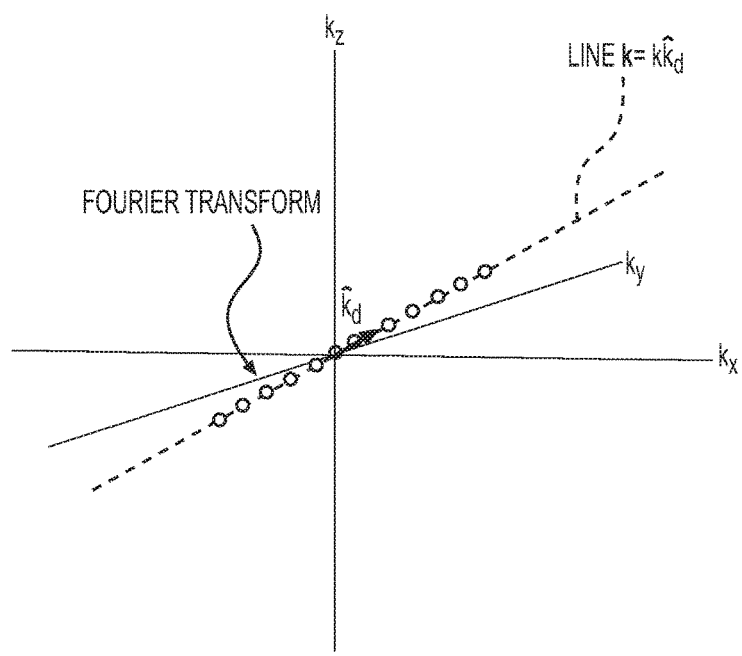

Assuming that the projection in d-space were completely filled (i.e., there were no missing data in the trumpet-like portions), it would be possible to go from d-space to k-space. This may be accomplished by interpolating d-space along radial lines, taking the 1D Fourier transform, and inserting the resulting values along radial lines in k-space. Interpolations in d-space are depicted in FIG. 8A, and the resulting values along radial line k are shown in k-space in FIG. 8B. By repeating this step while varying the orientation of the radial lines interpolated in d-space and then using 1D Fourier transform, all of k-space may be covered, and it may be possible to completely fill in k-space. The 3D image data may then be reconstructed from k-space by calculating the 3D inverse Fourier transform of the k-space data.

The new concept of d-space for handling non-parallel (e.g., divergent) projection ray lines and for the compression of projection image data makes it possible to more easily manipulate and reconstruct imaging data. This novel method also enables complex calculations to be performed more quickly in order to reconstruct 3D images from the CBCT projections, allowing for real-time tracking of data.

The missing trumpet data in d-space is a manifestation of the "incomplete" nature of CBCT reconstruction with a single gantry arc and is the reason why algorithms, for example, including the Feldkamp-Davis-Kress (FDK) algorithm, require approximations.

In practical digital applications, k-space is generally not evaluated out to infinity. Rather, a cut-off frequency may be used to limit the extent of k-space. A standard rule of thumb is to use a cut-off frequency that is at least equal to the Nyquist frequency, to avoid incurring aliasing effects. The Nyquist frequency in this case is defined as half of the inverse of the resolution of the image. For example, if the voxels of an image are 1 mm cube, then the Nyquist frequency is 0.5 cycles/mm. Thus, the radius of the missing trumpet data may have a maximum at the Nyquist frequency. In some embodiments, the missing data from the trumpet-shaped portion may be filled in via direct interpolation of neighboring points in d-space.

In radiotherapy applications, there may be an initial planning CT available that was previously acquired on a diagnostic-quality CT scanner (i.e., a traditional CT image that may not have the incomplete trumpet-data issue of a CBCT image, and thus may provide full k-space coverage). The planning CT may have been taken during pre-treatment, during patient preparation, or during earlier treatment sessions, for example. The planning CT may be converted into a d-space image by ray-tracing. In ray-tracing, a plurality of cone-beam projections may be simulated by setting up a plurality of ray lines with respect to the CT geometry. The CT pixels may be summed along each ray line to give a projection value for that ray-line. These values may then be inserted into d-space with the appropriate vector d (which is the vector connecting the origin and the closest point along the respective ray line).

Points on the converted d-space planning CT that fall within the missing trumpet portion of the d-space cone-beam projections may then be expressed as a function of other points in d-space. Missing CBCT data points in the trumpet portion may then be filled in using the determined planning CT relationship. While there are a number of different ways in which trumpet data may be filled in, the planning CT, once converted to d-space, may be used to "learn" how the missing trumpet portion should be fitted to the CBCT data in d-space. For example, one or more of an algebraic relationship, principal component analysis, machine learning algorithms, etc., may be used to fill in the missing trumpet data.

Figure 9A:
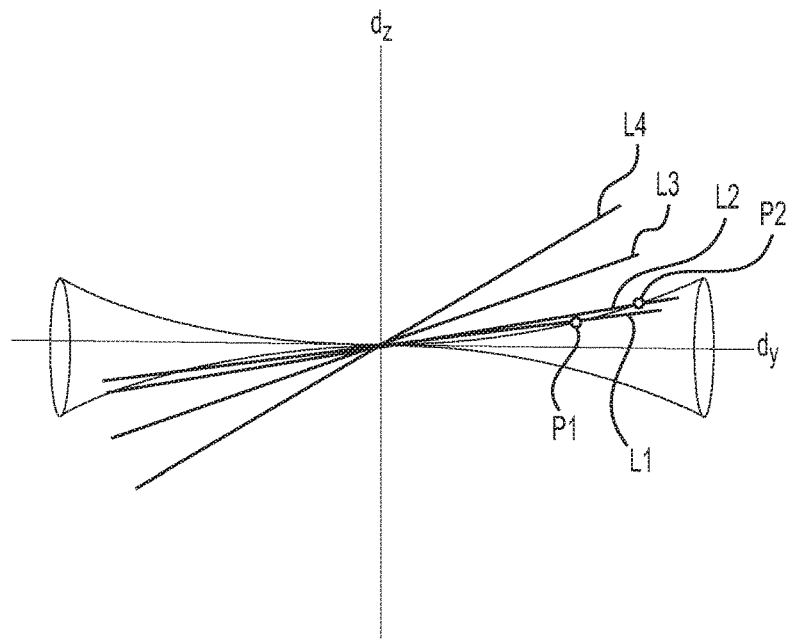
FIGS. 9A and 9B schematically depict an exemplary mathematical process that may be performed on imaging data in accordance with various embodiments of the present disclosure.
Figure 9B:
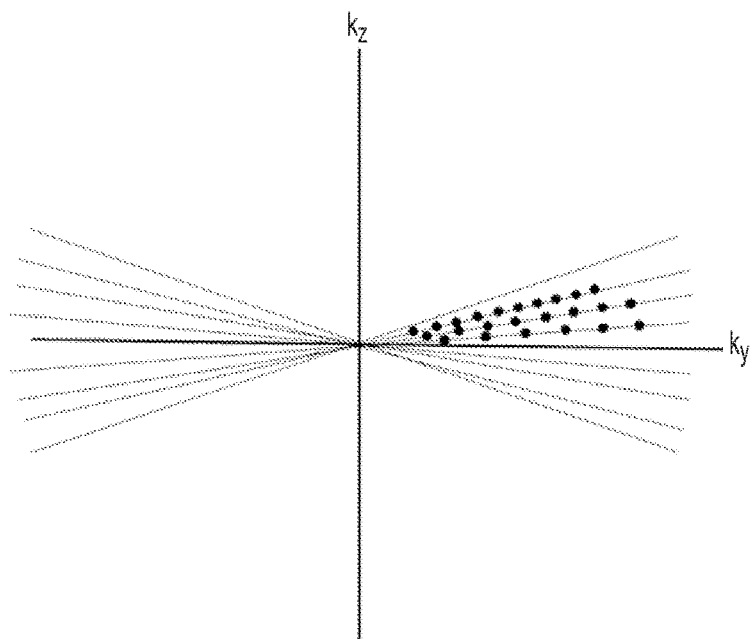

As radial lines in d-space are selected, many of the radial lines will not intersect with the missing trumpet data, for example, lines L3 and L4 in FIG. 9A. Data along lines L3 and L4 may be converted directly from d-space into k-space via 1D Fourier transform. Other lines may intersect with the missing trumpet region, for example, lines L1 and L2 (at points P1 and P2, respectively). Lines L1 and L2 may contribute partial data, up to the point at which they intersect with the trumpet portion. This may be equivalent to having a limited field of view for lines L1 and L2, which in the Fourier domain, may result in a reduced sample spacing. Stated mathematically, if the length of data along the line from the origin to the point at which the line intersects the trumpet region is L, then the sample spacing of the Fourier data in k-space along the corresponding radial line in k-space (e.g., of L1 or L2 that intersect the trumpet region) would be 1/L. As shown in FIG. 9B, the sampling interval along radial lines increases as the radial lines approach the $k_y$ axis. On the axis itself, the sample spacing approaches infinity, resulting in no data along the $k_y$ axis.

Accordingly, k-space may be filled even in the presence of missing data in d-space. In some embodiments, interpolation may then be carried out directly in k-space rather than in d-space. In some embodiments, the planning CT may first be converted to k-space to assist with interpolation of the CBCT data in k-space, analogously to the above description of interpolation in d-space. In some embodiments, the k-space data may not be interpolated, but a NUFFT algorithm may be used to directly calculate the inverse 3D Fourier transform on the non-uniformly spaced k-space points into the spatial domain to reconstruct the 3D image.

In some embodiments, interpolation in d-space to resample data along uniform lines prior to calculating the 1D Fourier transforms may cause artifacts. In such embodiments, a NUFFT algorithm may be used, or data from the planning CT image may be used to "learn" how to interpolate the projection data in a similar manner as described above.

One of ordinary skill in the art will recognize that there are a number of alternative ways of filling in the missing trumpet data, either in d-space or in k-space, each of which is embraced by the scope of this application.

Image Reconstruction

In exemplary embodiments of the present disclosure, real-time analysis of a current CBCT image may be performed in d-space in order to handle the existence of non-parallel rays. As discussed above, CBCT projections may first be converted into d-space, a plurality of converted projection 'bowls' may be combined, and the missing trumpet data may be filled in using various techniques. Yet, as the projections rotate around the y-axis, and new d-space data is filled in with each sequential bowl, only the current projection (a.k.a., the current bowl) is accurate in the sense that it represents the true, current location of the target region. Embodiments of the present disclosure also address ways to reconstruct 3D images in real time that address the issue of stale data.

Although d-space may be filled in by rotating the sequentially acquired projections around an axis, e.g., the y-axis, as described in reference to FIG. 7B, only one of the plurality of projections depicts the current, 'true' location of points in a target region. This is because all of the other projections imaged prior to the current projection were taken at preceding points in time, and the stale projections may no longer depict the current location and/or orientation of the target region. A planning CT image, referred to above, would also be considered a stale projection. Prior, stale projections may have been taken at earlier points during radiotherapy treatment. The question then becomes how to combine the stale and current projections to form an accurate, real-time 3D image.

Embodiments of the present disclosure reconstruct the CBCT image using a single, current projection as a "constraint" and use other, stale projections to fill in the missing information, i.e., to generate cine-CBCT images in real time during radiotherapy treatments. For example, the current projection may be used as a constraint (e.g., weighted at 100% to represent the known, true values) to which the stale images may be fitted. The 3D image generated should be 'consistent' with the current projection. In some embodiments, 'consistent' may mean that if a person ray-traces through the 3D image to calculate an artificial projection (sometimes referred to as a digitally reconstructed radiograph, or DRR), an exact reproduction of the measured projection would be obtained. In other embodiments, 'consistent' may include corrections to compensate for physical phenomena, such as scatter or beam hardening, or may mean the DRR and measured projections are equal within a threshold, or in some other measure of similarity.

Reconstruction of the stale and current d-space projections may occur either in d-space, in k-space, or in a combination of d-space and k-space, depending on the technique used. In embodiments of the disclosure, the current projection is used as a constraint, and the constraint may be placed on actual points in d-space or k-space. This differs from other techniques that have previously been developed, which have instead relied on constraints on projections in the spatial domain, which are difficult to impose without using iterative reconstruction principles and are computationally intensive, making them unfeasible for real-time applications.

The filling in of d-space (or of k-space, depending on which space reconstruction is performed in) may occur in a number of different ways. In one embodiment, phase may be used to reconstruct a 3D image. This may be referred to as 4D CBCT (3D+phase). This may be particularly useful when regular, rhythmic, and/or cyclical movements are being tracked, for example, movement of a target area impacted by breathing or by a heartbeat. The most relevant stale projections may be selected by selecting for projections that were taken at the same point in the cycle. For example, a respiration phase may be assigned to each stale projection, and only the projections that have a similar phase as the current projection may be used to fill in the missing information from the current projection. The assumption is that the position of the target region across projection images from the same point in the phase will be more similar with one another than would the position of the target region in projection images from different points in the phase.

There may be a number of different ways to assign a phase to each projection. For example, the center value of k-space of each projection image may be used as a surrogate for phase. Projections with the same or similar center values may be assumed to have been taken at the same phase, and because the phase may affect movement of the target region, it may be assumed that the location and/or orientation of the target region in a projection from a similar phase would be similar. As a result, the assumption is that the stale projections sharing a common center value of k-space with the current projection may have the most relevant target area location information for reconstructing the current projection image.

In some embodiments, a subset of stale projections may be used to first reconstruct a phase-binned 4D image, using traditional tomographic reconstruction techniques, or with some of the reconstruction methods disclosed herein. Each 3D bin of the 4D dataset may then be converted to k-space to generate a reference 4D k-space training set. A relationship may then be determined between each 2D k-space plane within the 4D k-space training set, and the corresponding 3D k-space image in the 4D k-space training set. Once this relationship is found, every time there is a new k-space "current" plane that is acquired, the determined relationship may be used to find the approximate 3D k-space image from the current k-space plane. In order to reduce dimensionality, principal component analysis (PCA) or independent component analysis (ICA) may be used on the 2D and 3D k-space data.

Other exemplary methods and techniques to combine a current plane with stale planes in k-space to fill in missing data may include using Bayesian filtering techniques and analysis, for example, Kalman Filters or Particle Filters. In some embodiments, compressed sensing techniques, sparsity, machine learning, deep learning, and/or principal components analysis (PCA) may be used, for example.

To further explore this concept, it may help to begin with a hypothetical situation in which we could assume the presence of parallel lines. The projection provides a 2D plane in d-space, and performing a 2D Fourier transformation may convert this data directly to a 2D plane in k-space. The values along this plane in k-space would be current and may act as a constraint to the full, 3D k-space data. The rest of the k-space data would then need to be estimated using previous, stale projections, which would also be represented as planes in k-space. These stale projections may be combined with the current projection in many different ways. For example, each plane may share a common intersection value, the center of k-space, which may oscillate throughout a given phase, e.g., with respiration. Those k-space planes with the closest matching intersection values may be selected and used to construct the rest of k-space. Inverse 3D Fourier transform may then be performed to generate a 3D image that corresponds to the current image, consistent with the current projection.

In practice, however, the lines are not parallel, and the parallel-beam mathematics break down. Rather than the projections generating a plane in d-space, each cone-beam projection generates a curved plane ('bowl') of data, as previously discussed in reference to FIG. 6B. This data may be directly converted to k-space data through Fourier transformation, since the bowl of data only intersects with radial lines in Fourier space at a single point. A bowl thus only provides a single Fourier component along intersecting radial lines. The distance, in d-space, between the perpendicular plane and the bowl may increase with distance away from the origin and is expressed by the equation: $s=\sqrt{(R^2+d^2)}-R$.

Figure 10A:
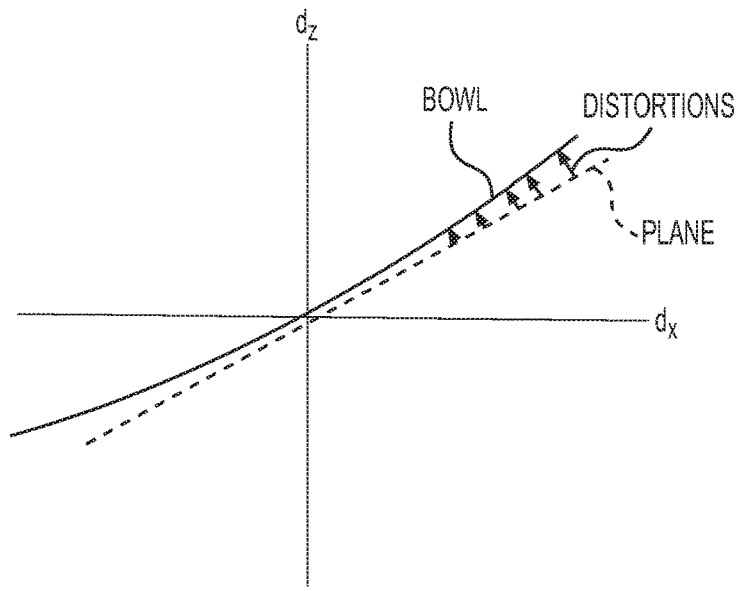
FIGS. 10A and 10B schematically depict an exemplary mathematical process that may be performed on imaging data in accordance with various embodiments of the present disclosure.
Figure 10B:
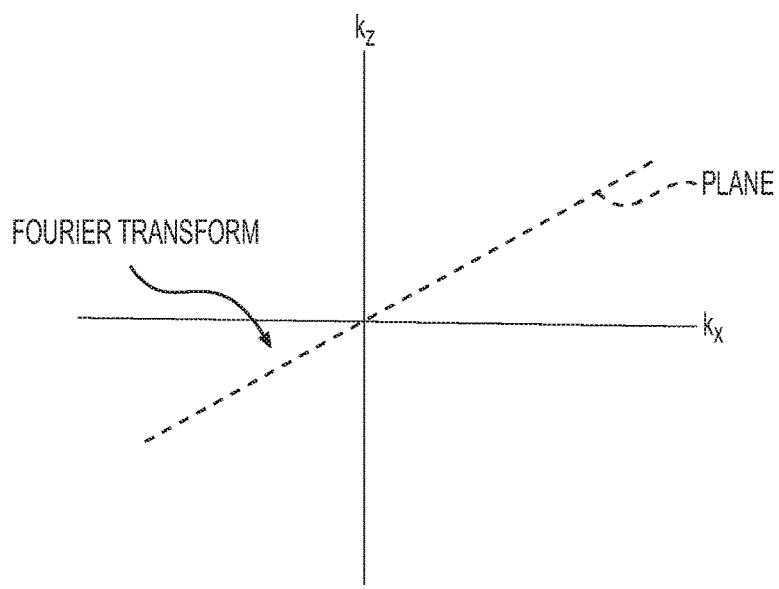

For radiotherapy applications, images are usually de-magnified to isocenter (the point of gantry rotation), which is typically in the range of approximately 80 cm to 120 cm, for example, 100 cm. At 10 cm, this results in a 0.5 mm distance between the plane and the bowl; at 20 cm away from central axis, which for many applications may be considered the maximum distance at the edge of the detector, the distance increases to 2 mm. In radiotherapy, bowls are very close to planes for good approximation with a second-order distortion away from a pure plane. FIGS. 10A and 10B show this relationship.

In some embodiments, the bowls may be approximated to be planes, and the second-order distortions may be neglected. Such embodiments may still yield good results for typical geometries in radiotherapy. The data in the spatial domain may be directly converted to a plane of data in k-space, as in the case for parallel-beam geometry described above.

In other embodiments, d-space data from the curved 'bowl' surface may be extrapolated to the corresponding pure plane. This may be achieved in some cases by using earlier, stale projection data in d-space to perform the extrapolation. In other embodiments, this may be achieved by using the planning CT, converted to d-space, to help 'learn' how data is distorted from bowls to planes. Once data has been extrapolated to the plane in d-space, 2D Fourier Transformation may be used to convert the data from d-space to k-space.

In yet other embodiments, the full, 3D image may first be estimated in d-space rather than in k-space. The values along the current bowl in d-space are current data and may be used as a constraint. The problem then becomes how to fill in the rest of d-space (rather than k-space). The previously acquired bowls, which are now stale, may be combined in an analogous manner as described above in reference to estimating the data in k-space. The filled d-space image may then converted to k-space, and inverse 3D Fourier transformation may result in a 3D image that corresponds to the current image, consistent with the current projection.

Other methods commonly included in CBCT reconstruction may also be incorporated in the disclosed embodiments, for example, geometric corrections to account for gantry sag, beam hardening, and scatter corrections may also be applied to embodiments of the present disclosure.

Exemplary Embodiment Assuming Parallel Lines

In some embodiments, however, it may be possible to assume that the rays of a CBCT are in fact parallel, rather than diverging. For example, if a smaller target is being radiated, then the small portion of ray lines hitting the target may be almost parallel with one another. For example, looking back to FIG. 6A, a small target located within only a portion of cone beam 418 of divergent rays may be hit by only a subset of divergent rays. The smaller subset of rays hitting the target may be almost parallel with one another, even though across the width of the entire cone beam, the rays are divergent. By sampling only a smaller portion of the cone beam, it may be possible to assume the existence of parallel lines. For example, the target may be located in only a portion of the overall image, e.g., at a center region of a cone beam or at the edge of the cone beam. Rather than reconstructing an image using the rays from the full cone beam, only a smaller portion of the image may be reconstructed using only the rays that hit the target, or hit a smaller region around the target. This may be useful, e.g., for looking at a specific target within a larger target region. While many of the embodiments disclosed herein reconstruct a current projection image based on the full cone-beam projection and thus must deal with divergent rays in d-space, in this embodiment, focusing on generating a narrower image using only a portion of the cone beam may allow for the assumption of parallel lines, since the subset of rays hitting that smaller portion may be relatively parallel with one another. This may also be useful if the target is moving within a small area, or if the main focus is on the movement of the target rather than the actual image of the target.

Because the subset of rays may be almost parallel to each other, parallel beam approximation may be used, and a small image may be generated around the target. Because the presence of parallel lines is assumed in this embodiment, it may not be necessary to convert the CBCT projection to d-space. Instead, the projection may be converted directly into k-space, as described above in reference to FIGS. 3A and 3B. Embodiments that do not assume parallel lines and instead work with divergent lines must first convert the current projection image into d-space to perform real-time assessment of the current image, and then may either remain in d-space or may be converted to k-space to fill in missing information using stale projection images while the current image is used as a constraint. By contrast, embodiments that instead assume the presence of parallel lines may not need to be converted into d-space and may instead be converted from the spatial domain directly into k-space, and real-time monitoring may be performed in k-space. Calculation of the evolving 3D image may occur in k-space, and the 3D image may be continuously converted into the spatial domain. "Continuous," as used herein, includes conversion that is ongoing and includes conversion that is ongoing but occurs at spaced apart times. For example, in some embodiments, conversion of the 3D image from k-space into the spatial domain may not be delayed until the entire 3D image is reconstructed and instead may occur as the 3D image evolves. Continuous conversion of the 3D image may allow for ongoing localization of the target region in order to compensate for movement of the target during radiotherapy.

Exemplary Embodiment Using MRI-Linac

Figure 11:
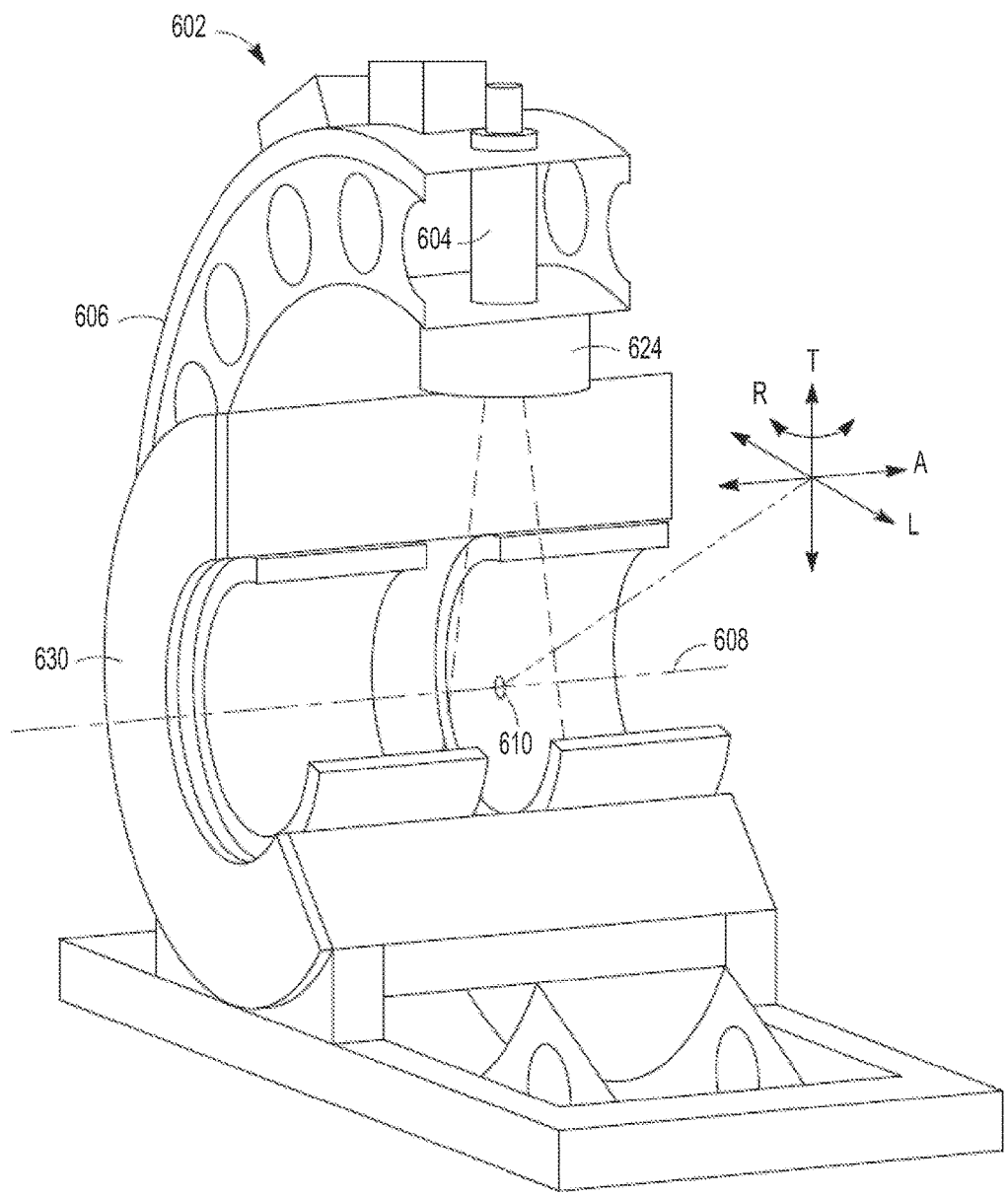
FIG. 11 depicts an exemplary radiotherapy device that may be used to implement various embodiments of the present disclosure.

In some embodiments of the present disclosure, an MRI-linac may be used instead of a conventional linac with CBCT imaging. FIG. 11 depicts a partially cut-away view of a combined radiation therapy system 602 and nuclear magnetic resonance (MR) imaging system 630. MR imaging system 630 may define a bore extending along an axis (A), and radiation therapy system 602 may include a radiation therapy output 604 configured to direct a radiation therapy beam 608 towards an isocenter 610 within the bore. Radiation therapy output 604 may include a collimator 624, which may control and/or shape radiation therapy beam 608 to direct beam 608 to a target region within a patient. The patient may be supported by a surface, for example, a platform positionable along one or more of an axial direction (A), a lateral direction (L), or a transverse direction (T). One or more portions of radiation therapy system 602 may be mounted on a gantry 606; for example, radiation therapy output 604 may rotate along gantry 606 about axis A.

As opposed to CBCT imaging, MR imaging is unique in that it gathers data directly in k-space. Whereas some embodiments of the disclosure discussed above convert cone-beam projection images into d-space and then eventually to k-space, MRI captures images directly into k-space. Accordingly, in MRI embodiments, real-time monitoring may be performed in k-space. As described above in reference to other embodiments, the current image in k-space may be used as a constraint, and other, stale images may be used to reconstruct a real-time 3D image in k-space representative of the true, current location of the target region. The reconstructed 3D k-space image may then be converted via Fourier transform into the spatial domain and may be used to monitor the movement of the target region within a patient and to control, and/or alter the delivery of radiotherapy depending on the detected movement.

As described above, calculation of the evolving 3D image may occur in k-space, and the 3D image may be continuously converted into the spatial domain. "Continuous," as used herein, means that in some embodiments, conversion of the 3D image from k-space into the spatial domain may not be delayed until the entire 3D image is reconstructed. Instead, conversion may occur as the 3D image evolves. Continuous conversion of the 3D image may allow for ongoing localization of the target region in order to compensate for movement of the target during radiotherapy.

Embodiments of the present disclosure, as described above, may allow a full, 3D soft-tissue image to be calculated that continuously evolves in real time. Intrafractional motion of target and organs at risk may thus be detected in real time, enabling gating and MLC tracking during radiation treatment. In some embodiments, the use of fiducials may not be required. Eventually, full deformation vector fields may be calculated in real time to enable real-time adaptive radiotherapy. Embodiments of the present disclosure may be used in conjunction with any suitable radiation therapy device, e.g., conventional linacs, MRI-linacs, Gamma Knife systems, or any other suitable radiation delivery systems.

Exemplary Medical Systems for Performing Processes of the Disclosure

Figure 12:
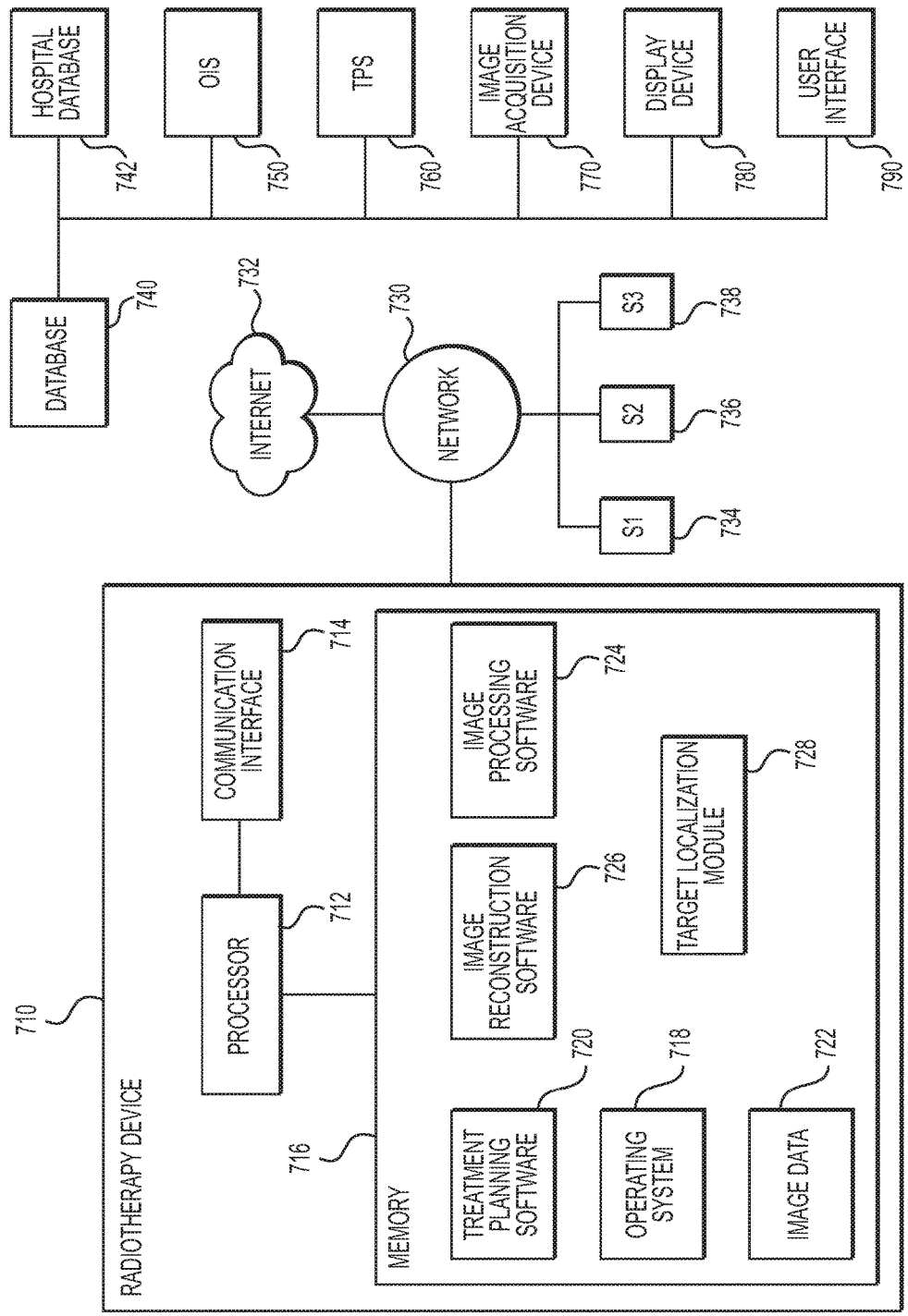
FIG. 12 depicts an exemplary system that may be used to provide real-time imaging guidance in accordance with various embodiments of the present disclosure.

As discussed above in reference to FIGS. 1A, 1B, and 1C, the image processing disclosed herein may be carried out on any suitable computer or medical system. FIG. 12 illustrates an exemplary radiotherapy system 700 for performing real-time target localization and tracking during radiation therapy treatment using the novel techniques described above. Radiotherapy system 700 may include a radiation therapy device 710 connected to a network 730 that is connected to an internet 732. Network 730 may connect radiation therapy device 710 with one or more of a database 740, a hospital database 742, an oncology information system (OIS) 750 (e.g., which may include patient information), a treatment planning system (TPS) 760 (e.g., for generating radiation therapy treatment plans to be carried out by the radiotherapy device 710), an image acquisition device 770, a display device 780 and/or a user interface 790. Each of these components may be housed in the same region as radiotherapy device 710 or may be remote from radiotherapy device 710, for example, connected to radiotherapy device 710 by the Internet or network connection.

Radiotherapy device 710 may include a processor 712, a memory device 716, and a communication interface 714. Memory device 716 may store computer executable instructions for one or more of an operating system 718, treatment planning software 720, image processing software 724, image reconstruction software 726, a target localization module 728, and/or any other computer executable instructions to be executed by processor 712. These executable instructions may configure processor 712 to execute the steps of the exemplary embodiments described above, including, e.g., the conversion of CBCT projections into d-space, the reconstruction of 3D or 4D CBCT or MRI images in one or more of d-space or k-space, the conversion of projection images from d-space to k-space, and/or the conversion of projection images from k-space to the spatial domain.

Processor 712 may be communicatively coupled to memory device 716, and processor 712 may be configured to execute computer executable instructions stored thereon. For example, processor 712 may execute image processing software 724 and/or image reconstruction software 726 to implement functionalities of each and may combine these with the functionalities of target localization module 728 in order to determine a location of the target in a patient during administration of radiotherapy. In addition, processor 712 may execute treatment planning software 720 (e.g., Monaco® software manufactured by Elekta) that may interface with image processing software 724, image reconstruction software 726, and/or target localization module 728.

Processor 712 may be a processing device, include one or more general-purpose processing devices such as a microprocessor, central processing unit (CPU), graphics processing unit (GPU), an accelerated processing unit (APU), or other suitable equipment. In some embodiments, processor 712 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 712 may also be one or more special-purpose processing devices, such as an application specific integrated circuit (ASIC), a field programmable gate array (FPGA), a digital signal processor (DSP), a System on a Chip (SoC), or the like. As would be appreciated by those skilled in the art, in some embodiments, processor 712 may be a special-purpose processor, rather than a general-purpose processor, for example, one typically used for medical imaging, and therefore may have one or more graphical processing units and accelerated processing units. Processor 712 may include one or more known processing devices, such as a microprocessor from the Pentium™, Core™, Xeon™, or Itanium® family manufactured by Intel™, the Turion™ Athlon™ Sempron™ Opteron™ FX™ Phenom™ family manufactured by AMD™, or any of various processors manufactured by Sun Microsystems, or other suitable processors. Processor 712 may also include graphical processing units, such as a GPU from the GeForce®, Quadro®, Tesla® family manufactured by Nvidia™ GMA, Iris™ family manufactured by Intel™, or the Radeon™ family manufactured by AMD™, or other suitable processors. Processor 712 may in some embodiments include accelerated processing units such as the Desktop A-4(6, 8) Series manufactured by AMD™ or the Xeon Phi™ family manufactured by Intel™. In one embodiment, processor 712 may be configured to process large amounts of imaging data and/or signal data in real time, where "real time" means that the input data is processed at a speed that allows output or feedback to be made available during a radiotherapy procedure. The disclosed embodiments are not limited to any type of processor(s) otherwise configured to meet the computing demands of identifying, analyzing, maintaining, generating, and/or providing large amounts of imaging data or manipulating such imaging data to localize and track a target or to manipulate any other type of data consistent with the disclosed embodiments. In addition, the term "processor" may include more than one processor, for example, a multi-core design or a plurality of processors each having a multi-core design. Processor 712 may execute sequences of computer program instructions stored in memory 716 to perform the various operations, processes, and methods described above.

Memory device 716 may store image data 722 (e.g., CT, CBCT, MRI, etc.) received from image acquisition device 770 or another suitable image acquisition device. Memory device 716 may also store any other suitable type of data/information in any format that may be used by radiotherapy device 710 to perform operations consistent with the disclosed embodiments. Memory device 716 may include a read-only memory (ROM), a flash memory, a random access memory (RAM), a dynamic random access memory (DRAM), such as synchronous DRAM (SDRAM) or Rambus DRAM, a static memory (e.g., flash memory, static random access memory), etc., on which computer executable instructions may be stored in any format. In an exemplary embodiment, memory device 716 may be a plurality of memory devices. In some embodiments, memory device 716 may include a plurality of memory devices that are remotely located but accessible to processor 712. The computer program instructions may be accessed by processor 712, read from the ROM, or any other suitable memory location, and loaded into the RAM for execution by processor 712. For example, memory 716 may store one or more software applications. Software applications stored in memory 716 may include, for example, an operating system 718 for common computer systems, as well as for software-controlled devices. Further, memory 716 may store an entire software application or only a part of a software application that is executable by processor 712. For example, memory device 716 may store one or more radiation therapy treatment plans generated by treatment planning system 760 and/or may store treatment planning software 720.

In some embodiments, memory device 716 may include a machine-readable storage medium. Exemplary embodiments may include a single medium or may include multiple media (e.g., a centralized or distributed database, and/or associated caches and servers) that store the one or more sets of computer executable instructions or data. The term "machine-readable storage medium" refers to any medium that is capable of storing or encoding a set of instructions for execution by the machine and that cause the machine to perform any one or more of the methodologies of the present disclosure. The term "machine readable storage medium" shall accordingly be defined as including, but not be limited to, solid-state memories, optical and magnetic media, or the like. For example, memory 716 may be one or more volatile, non-transitory, or non-volatile tangible computer-readable media.

Radiotherapy device 710 may communicate with a network 730 via a communication interface 714, which may be communicatively coupled to processor 712 and memory 716. Communication interface 714 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), or other suitable connections. Communication interface 714 may include one or more digital and/or analog communication devices that permit radiotherapy device 710 to communicate with other machines and devices, such as remotely located components, via a network 730.

Network 730 may provide the functionality of a local area network (LAN), a wireless network, a cloud computing environment (e.g., software as a service, platform as a service, infrastructure as a service, etc.), a client-server, a wide area network (WAN), or the like. Therefore, network 730 may allow data transmission between radiotherapy device 710 and a number of other devices, including TPS 760, OIS 750, and image acquisition device 770. Further, data generated by TPS 760, OIS 750, and image acquisition device 770 may be stored in memory 716, database 740, and/or hospital database 742. The data may be transmitted/received via network 730 and through communication interface 714 in order to be accessed by processor 712.

Exemplary Methods of the Disclosure

Figure 13:
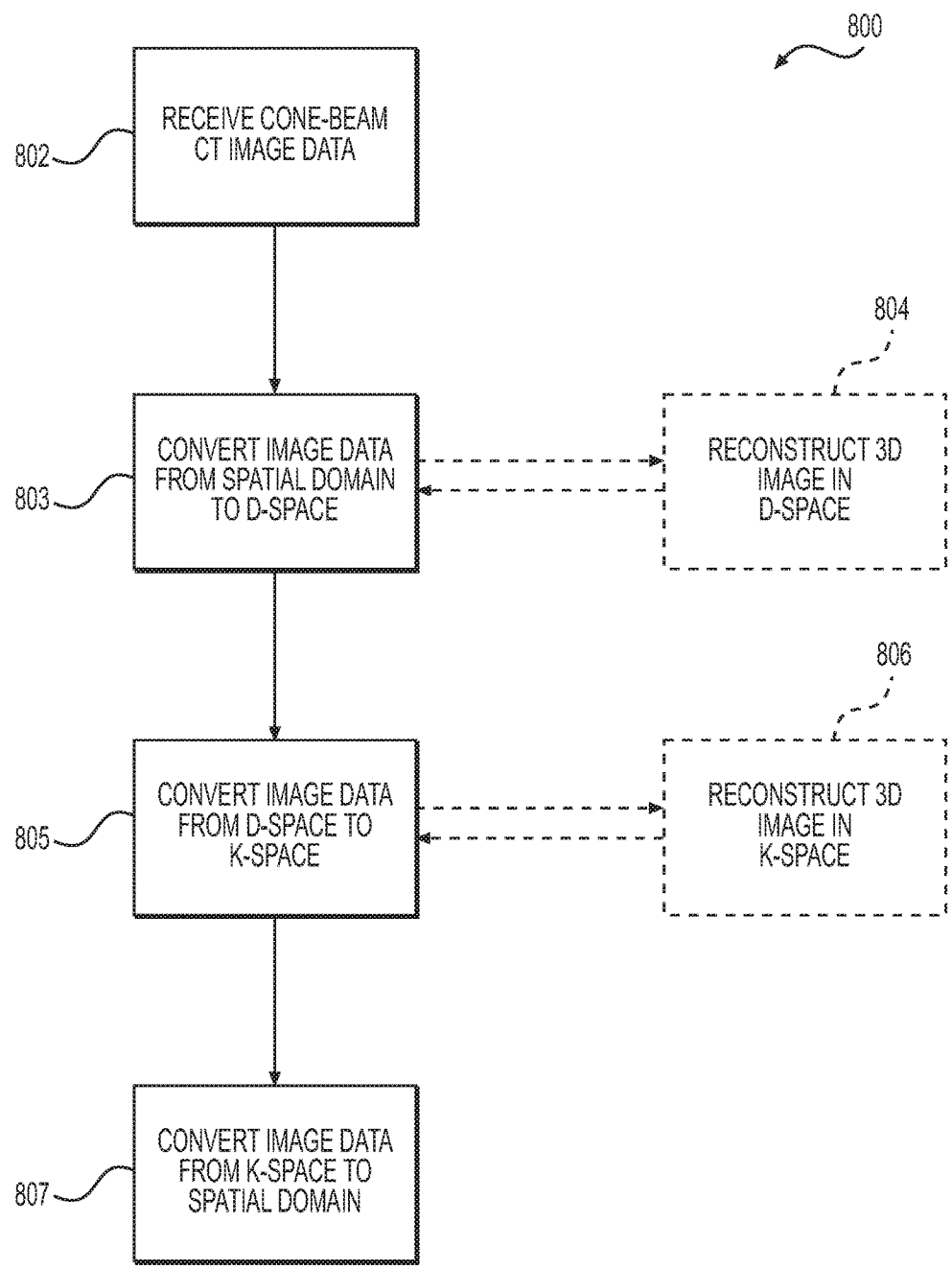
FIG. 13 is a flow chart depicting an exemplary method in accordance with the present disclosure.
Figure 14:
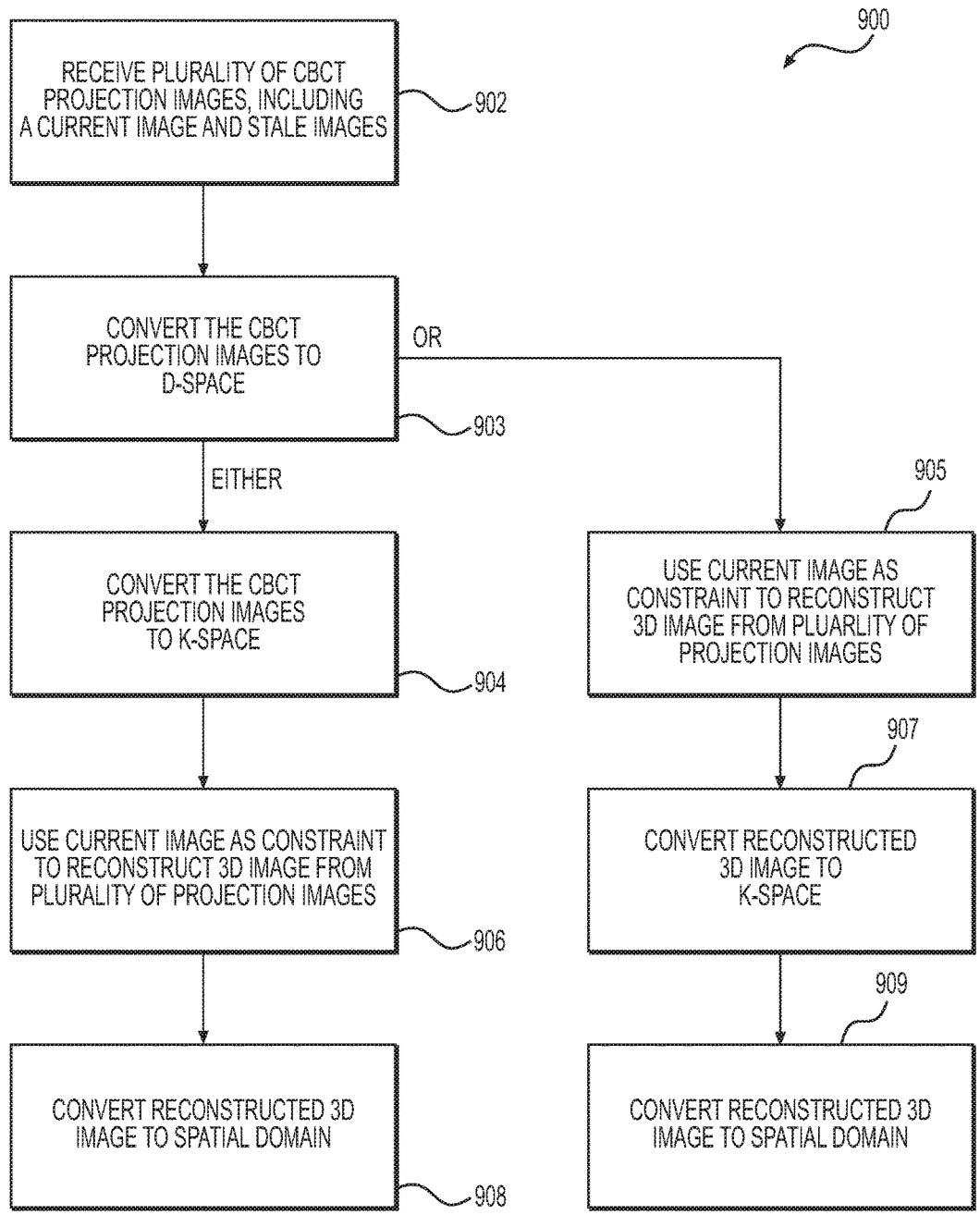
FIG. 14 is a flow chart depicting an exemplary method in accordance with the present disclosure.
Figure 15:
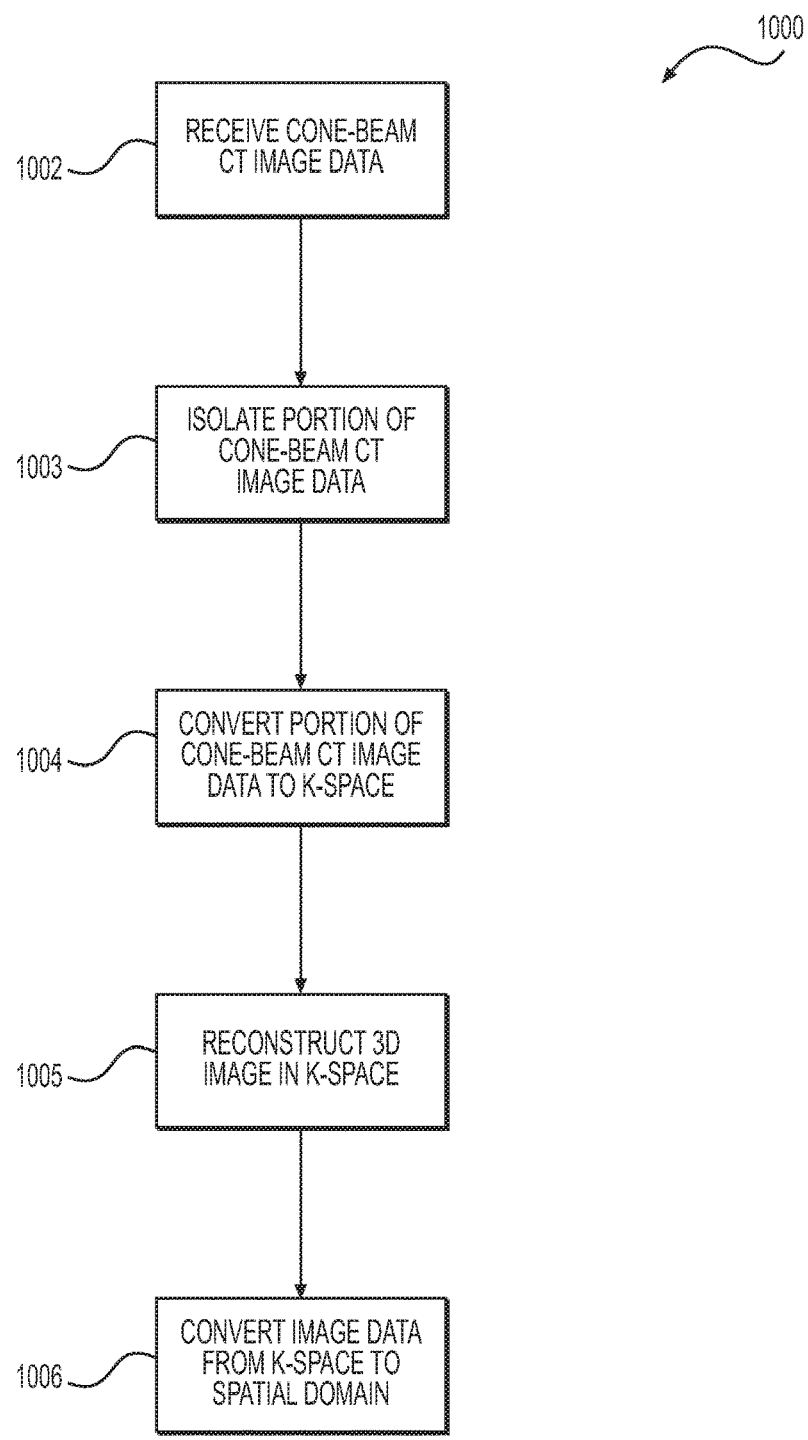
FIG. 15 is a flow chart depicting another exemplary method in accordance with the present disclosure.

FIGS. 13 through 15 are flow charts depicting exemplary methods of the disclosure that may be performed by the medical systems described above (e.g., in any of FIGS. 1A, 1B, 1C, and/or 12) or any other suitable system. In FIGS. 13 through 15, the receiving steps may be performed by any suitable component, e.g., by imaging and control system 111 (including one or more of controller 115 and database 117), by TAS 120 (e.g., by one or more of input/output circuit 122, memory circuit 124, and processor circuit 126), by radiotherapy device 710 (e.g., by one or more of processor 712, communication interface 714, memory 716—including any components within memory 716), or any other device or component of a system described herein.

FIG. 13 depicts a method 800 in which CBCT image data is received (step 802), and the image data is then converted into d-space (step 803). Once converted, the image data may be reconstructed into a 3D image in d-space (optional step 804). Optionally, the image data may be converted from d-space to k-space (step 805) and then reconstructed into a 3D image in k-space (optional step 806). Reconstruction of the 3D image may occur in either d-space, or k-space, or both d-space and k-space (e.g., some reconstruction could occur in each of the non-spatial domains). Ultimately, the image data may be converted from k-space to the spatial domain.

FIG. 14 depicts a method 900 according to another embodiment. In the method of FIG. 14, a plurality of CBCT projection images is received (step 902). The plurality of CBCT images includes a current image and a plurality of stale images. Each of the plurality of CBCT projection images is converted to d-space (step 903). Once converted to d-space, the plurality of images may either be converted to k-space (step 904), or the current image may be used as a constraint to reconstruct a 3D image from the plurality of projection images in d-space (step 905). If step 905 is performed, then the reconstructed image may be converted to k-space (step 907) and then may be converted to the spatial domain (step 909). If step 904 is chosen, then the current image may be used as a constraint to reconstruct a 3D image from the plurality of projection images in k-space (step 906), and then the reconstructed 3D image may be converted to the spatial domain.

FIG. 15 depicts another exemplary method 1000. In method 1000, CBCT image data may be received (step 1002), and a portion of the CBCT image data may be isolated out (step 1003). The portion of CBCT image data may then be converted to k-space (step 1004). A 3D image may be reconstructed in k-space (step 1005), and the reconstructed 3D image may then be converted from k-space to the spatial domain (step 1006).

The many features and advantages of the present disclosure are apparent from the detailed specification, and thus, it is intended by the appended claims to cover all such features and advantages of the present disclosure that fall within the true spirit and scope of the disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A system for generating three-dimensional images of a target region of a patient, the system comprising:
at least one computer system configured to:
receive a non-parallel projection image of the target region of the patient generated using a projection beam having a plurality of rays;
convert the non-parallel projection image into a non-spatial domain, the non-parallel projection image, generated using the projection beam having the plurality of rays, being converted into the non-spatial domain based on vectors, perpendicular to respective ones of the rays, the vectors formed between an isocenter of the projection beam and respective points along respective ones of the rays that are closest in proximity to the isocenter than other points along the respective ones of the rays;
reconstruct a three-dimensional image from at least the non-parallel projection image in the non-spatial domain; and
convert the reconstructed three-dimensional image from the non-spatial domain to the spatial domain.

2. The system of claim 1, wherein the non-parallel projection image is one of a plurality of non-parallel projection images that are a plurality of cone-beam computed tomography projection images.

3. The system of claim 1, wherein the non-parallel projection image is one of a plurality of non-parallel projection images that includes one current projection image obtained at a first time period and a plurality of stale projection images obtained at one or more time periods before the first time period.

4. The system of claim 3, wherein the one current projection image is used as a constraint to which the plurality of stale projection images are fitted during reconstruction of the three-dimensional image in the non-spatial domain.

5. The system of claim 1, wherein the non-spatial domain is a first non-spatial domain, the at least one computer system further being configured to convert the reconstructed three-dimensional image into a second non-spatial domain before converting the reconstructed three-dimensional image into the spatial domain.

6. They system of claim 5, wherein the first non-spatial domain is d-space, and the second non-spatial domain is k-space.

7. The system of claim 1, wherein the non-spatial domain is a second non-spatial domain, the at least one computer system further being configured to convert the non-parallel projection image to a first non-spatial domain before converting the non-parallel projection image into the second non-spatial domain.

8. The system of claim 7, wherein the first non-spatial domain is d-space, and the second non-spatial domain is k-space.

9. The system of claim 1, wherein the target region includes a tumor.

10. The system of claim 1, wherein the system further comprises a linear accelerator configured to acquire the non-parallel projection image and transmit the image to the computer system.

11. The system of claim 10, wherein the at least one computer system is further configured to:
modify a characteristic of the linear accelerator based on a location of a target within the target region in the reconstructed three-dimensional image.

12. The system of claim 11, wherein the characteristic of the linear accelerator is a characteristic of a beam of radiation output from the linear accelerator.

13. The system of claim 11, wherein the characteristic of the linear accelerator is an orientation of at least a portion of the linear accelerator relative to the patient.

14. The system of claim 1, wherein the at least one computer system is further configured to:
modify a treatment plan based on a location of a target within the target region in the reconstructed three-dimensional image.

15. The system of claim 1, wherein the at least one computer system is further configured to:
receive one or more second non-parallel projection images of the target region of the patient;
convert the one or more second non-parallel projection images into the non-spatial domain;
reconstruct a second three-dimensional image from at least the one or more second non-parallel projection images in the non-spatial domain; and
convert the reconstructed second three-dimensional image from the non-spatial domain to the spatial domain.

16. The system of claim 1, wherein the at least one computer system is configured to receive, convert, reconstruct, and convert in real time.

17. A computer-implemented method for generating three-dimensional images of a target region of a patient, the method comprising:
   receiving a non-parallel projection image of the target region of the patient generated using a projection beam having a plurality of rays;
   converting the non-parallel projection image into a non-spatial domain, the non-parallel projection image, generated using the projection beam having the plurality of rays, being converted into the non-spatial domain based on vectors, perpendicular to respective ones of the rays, the vectors formed between an isocenter of the projection beam and respective points along respective ones of the rays that are closest in proximity to the isocenter than other points along the respective ones of the rays;
   reconstructing a three-dimensional image from at least the non-parallel projection image in the non-spatial domain; and
   converting the reconstructed three-dimensional image from the non-spatial domain to the spatial domain.

18. The method of claim 17, wherein the non-parallel projection image is one of a plurality of non-parallel projection images that are a plurality of cone-beam computed tomography projection images.

19. The method of claim 17, wherein the non-parallel projection image is one of a plurality of non-parallel projection images that includes one current projection image obtained at a first time period and a plurality of stale projection images obtained at one or more time periods before the first time period.

20. The method of claim 19, wherein the one current projection image is used as a constraint to which the plurality of stale projection images are fitted when reconstructing the three-dimensional image in the non-spatial domain.

21. The method of claim 17, wherein the non-spatial domain is a first non-spatial domain, the method further comprising:
   converting the reconstructed three-dimensional image into a second non-spatial domain before converting the reconstructed three-dimensional image into the spatial domain.

22. They method of claim 21, wherein the first non-spatial domain is d-space, and the second non-spatial domain is k-space.

23. The method of claim 17, wherein the non-spatial domain is a second non-spatial domain, the method further comprising converting the non-parallel projection image to a first non-spatial domain before converting the non-parallel projection image into the second non-spatial domain.

24. The method of claim 23, wherein the first non-spatial domain is d-space, and the second non-spatial domain is k-space.

25. The method of claim 17, wherein the target region includes a tumor.

26. The method of claim 17, further comprising:
   modifying a treatment plan to be delivered by a medical device based on a location of a target within the target region in the reconstructed three-dimensional image.

27. The method of claim 17, further comprising:
   receiving one or more second non-parallel projection images of the target region of the patient;
   converting the one or more second plurality of non-parallel projection images into the non-spatial domain;
   reconstructing a second three-dimensional image from the one or more second non-parallel projection images in the non-spatial domain; and
   converting the reconstructed second three-dimensional image from the non-spatial domain to the spatial domain.

28. The method of claim 17, wherein each of the receiving, converting, reconstructing, and converting are performed in real time.

29. A non-transitory computer-readable medium storing instructions that, when executed by a processor, cause the processor to perform a method of generating three-dimensional images of a target region of a patient, the method comprising:
   receiving a non-parallel projection image of the target region of the patient generated using a projection beam having a plurality of rays;
   converting the non-parallel projection image into a non-spatial domain, the non-parallel projection image, generated using the projection beam having the plurality of rays, being converted into the non-spatial domain based on vectors, perpendicular to respective ones of the rays, the vectors formed between an isocenter of the projection beam and respective points along respective ones of the rays that are closest in proximity to the isocenter than other points along the respective ones of the rays;
   reconstructing a three-dimensional image from at least the non-parallel projection image in the non-spatial domain; and
   converting the reconstructed three-dimensional image from the non-spatial domain to the spatial domain.

30. The method of claim 29, wherein the non-parallel projection image is one of a plurality of non-parallel projection images that are a plurality of cone-beam computed tomography projection images.

31. The method of claim 29, wherein the non-parallel projection image is one of a plurality of non-parallel projection images that includes one current projection image obtained at a first time period and a plurality of stale projection images obtained at one or more time periods before the first time period.

32. The method of claim 31, wherein the one current projection image is used as a constraint to which the plurality of stale projection images are fitted when reconstructing the three-dimensional image in the non-spatial domain.

33. The method of claim 29, wherein the non-spatial domain is a first non-spatial domain, the method further comprising:
   converting the reconstructed three-dimensional image into a second non-spatial domain before converting the reconstructed three-dimensional image into the spatial domain.

34. They method of claim 33, wherein the first non-spatial domain is d-space, and the second non-spatial domain is k-space.

35. The method of claim 29, wherein the non-spatial domain is a second non-spatial domain, the method further comprising converting the non-parallel projection image to a first non-spatial domain before converting the non-parallel projection image into the second non-spatial domain.

36. The method of claim 35, wherein the first non-spatial domain is d-space, and the second non-spatial domain is k-space.

37. The method of claim 29, wherein the target region includes a tumor.

38. The method of claim 29, further comprising:

modifying a treatment plan to be delivered by a medical device based on a location of a target within the target region in the reconstructed three-dimensional image.

39. The method of claim 29, further comprising:
receiving one or more second non-parallel projection images of the target region of the patient;
converting the one or more second non-parallel projection images into the non-spatial domain;
reconstructing a second three-dimensional image from the one or more second non-parallel projection images in the non-spatial domain; and
converting the reconstructed second three-dimensional image from the non-spatial domain to the spatial domain.

40. The method of claim 29, wherein each of the receiving, converting, reconstructing, and converting are performed in real time.

41. A system for generating three-dimensional images of a target region of a patient, the system comprising:
at least one computer system configured to:
receive cone-beam computed tomography imaging data having a plurality of rays;
convert the imaging data from a spatial domain into a first non-spatial domain, the imaging data, being converted into the non-spatial domain based on vectors, perpendicular to respective ones of the rays, the vectors formed between an isocenter of the cone-beam and respective points along respective ones of the rays that are closest in proximity to the isocenter than other points along the respective ones of the rays;
convert the imaging data from the first non-spatial domain into a second non-spatial domain;
reconstruct a three-dimensional image from the imaging data in at least one of the first non-spatial domain and the second non-spatial domain; and
convert the reconstructed three-dimensional image from the second non-spatial domain to the spatial domain.

42. The system of claim 41, wherein the first non-spatial domain is d-space, and the second non-spatial domain is k-space.

43. The system of claim 41, wherein the imaging data includes a plurality of cone-beam computed tomography projections.

44. A computer-implemented method for generating three-dimensional images of a target region of a patient, the method comprising:
receiving cone-beam computed tomography imaging data having a plurality of rays;
converting the imaging data from a spatial domain into a first non-spatial domain, the imaging data, being converted into the non-spatial domain based on vectors, perpendicular to respective ones of the rays, the vectors formed between an isocenter of the cone-beam and respective points along respective ones of the rays that are closest in proximity to the isocenter than other points along the respective ones of the rays;
converting the imaging data from the first non-spatial domain into a second non-spatial domain;
reconstructing a three-dimensional image from the imaging data in at least one of the first non-spatial domain and the second non-spatial domain; and
converting the reconstructed three-dimensional image from the second non-spatial domain to the spatial domain.

45. The method of claim 44, wherein the first non-spatial domain is d-space, and the second non-spatial domain is k-space.

46. The method of claim 44, wherein the imaging data includes a plurality of cone-beam computed tomography projections.

47. A non-transitory computer-readable medium storing instructions that, when executed by a processor, cause the processor to perform a method of generating three-dimensional images of a target region of a patient, the method comprising:
receiving cone-beam computed tomography imaging data having a plurality of rays;
converting the imaging data from a spatial domain into a first non-spatial domain, the imaging data, being converted into the non-spatial domain based on vectors, perpendicular to respective ones of the rays, the vectors formed between an isocenter of the cone-beam and respective points along respective ones of the rays that are closest in proximity to the isocenter than other points along the respective ones of the rays;
converting the imaging data from the first non-spatial domain into a second non-spatial domain;
reconstructing a three-dimensional image from the imaging data in at least one of the first non-spatial domain and the second non-spatial domain; and
converting the reconstructed three-dimensional image from the second non-spatial domain to the spatial domain.

48. The method of claim 47, wherein the first non-spatial domain is d-space, and the second non-spatial domain is k-space.

49. The method of claim 47, wherein the imaging data includes a plurality of cone-beam computed tomography projections.

50. A system for generating three-dimensional images of a target region of a patient, the system comprising:
at least one computer system configured to:
receive a plurality of non-parallel projection images of the target region of the patient;
convert the plurality of non-parallel projection images into a first representation in a three-dimensional non-spatial domain;
convert the first representation in the three-dimensional non-spatial domain to a second representation in a one-dimensional non-spatial domain;
reconstruct a three-dimensional image from the first and second representations; and
convert the reconstructed three-dimensional image from the non-spatial domain to the spatial domain.

51. The system of claim 50, wherein the at least one computer system is configured to receive and reconstruct in real time.

52. The system of claim 50, wherein the non-parallel projection image is one of a plurality of non-parallel projection images that includes one current projection image obtained at a first time period and a plurality of stale projection images obtained at one or more time periods before the first time period.

53. A method for generating three-dimensional images of a target region of a patient, the method comprising:
receiving a plurality of non-parallel projection images of the target region of the patient;
converting the plurality of non-parallel projection images into a first representation in a three-dimensional non-spatial domain;

converting the first representation in the three-dimensional non-spatial domain to a second representation in a one-dimensional non-spatial domain;

reconstructing a three-dimensional image from the first and second representations; and converting the reconstructed three-dimensional image from the non-spatial domain to the spatial domain.

54. The method of claim 53, wherein the receiving and reconstructing are performed in real time.

55. The method of claim 53, wherein the non-parallel projection image is one of a plurality of non-parallel projection images that includes one current projection image obtained at a first time period and a plurality of stale projection images obtained at one or more time periods before the first time period.

56. A non-transitory computer-readable medium storing instructions that, when executed by a processor, cause the processor to perform a method of generating three-dimensional images of a target region of a patient, the method comprising:

receiving a plurality of non-parallel projection images of the target region of the patient;

converting the plurality of non-parallel projection images into a first representation in a three-dimensional non-spatial domain;

converting the first representation in the three-dimensional non-spatial domain to a second representation in a one-dimensional non-spatial domain;

reconstructing a three-dimensional image from the first and second representations; and converting the reconstructed three-dimensional image from the non-spatial domain to the spatial domain.

57. The method of claim 56, wherein the receiving and reconstructing are performed in real time.

58. The method of claim 56, wherein the non-parallel projection image is one of a plurality of non-parallel projection images that includes one current projection image obtained at a first time period and a plurality of stale projection images obtained at one or more time periods before the first time period.

59. A system for generating three-dimensional images of a target region of a patient, the system comprising:

at least one computer system configured to:

receive a plurality of non-parallel projection images of the target region of the patient;

convert the plurality of non-parallel projection images into d-space and k-space non-spatial domains;

reconstruct a three-dimensional image from the plurality of non-parallel projection images in the d-space and k-space non-spatial domains; and convert the reconstructed three-dimensional image from the d-space and k-space non-spatial domains to the spatial domain.

60. The system of claim 59, wherein the at least one computer system is configured to receive and reconstruct in real time.

61. The system of claim 59, wherein the non-parallel projection image is one of a plurality of non-parallel projection images that includes one current projection image obtained at a first time period and a plurality of stale projection images obtained at one or more time periods before the first time period.

62. A method for generating three-dimensional images of a target region of a patient, the method comprising:

receiving a plurality of non-parallel projection images of the target region of the patient;

converting the plurality of non-parallel projection images into d-space and k-space non-spatial domains;

reconstructing a three-dimensional image from the plurality of non-parallel projection images in the d-space and k-space non-spatial domains; and converting the reconstructed three-dimensional image from the d-space and k-space non-spatial domains to the spatial domain.

63. The method of claim 62, wherein the receiving and reconstructing are performed in real time.

64. The method of claim 62, wherein the non-parallel projection image is one of a plurality of non-parallel projection images that includes one current projection image obtained at a first time period and a plurality of stale projection images obtained at one or more time periods before the first time period.

65. A non-transitory computer-readable medium storing instructions that, when executed by a processor, cause the processor to perform a method of generating three-dimensional images of a target region of a patient, the method comprising:

receiving a plurality of non-parallel projection images of the target region of the patient;

converting the plurality of non-parallel projection images into d-space and k-space non-spatial domains;

reconstructing a three-dimensional image from the plurality of non-parallel projection images in the d-space and k-space non-spatial domains; and converting the reconstructed three-dimensional image from the d-space and k-space non-spatial domains to the spatial domain.

66. The method of claim 65, wherein the receiving and reconstructing are performed in real time.

67. The method of claim 65, wherein the non-parallel projection image is one of a plurality of non-parallel projection images that includes one current projection image obtained at a first time period and a plurality of stale projection images obtained at one or more time periods before the first time period.

* * * * *

UNITED STATES PATENT AND TRADEMARK OFFICE
CERTIFICATE OF CORRECTION

| | | |
|---|---|---|
| PATENT NO. | : 10,134,155 B2 | Page 1 of 1 |
| APPLICATION NO. | : 15/357193 | |
| DATED | : November 20, 2018 | |
| INVENTOR(S) | : Martin Emile Lachaine | |

It is certified that error appears in the above-identified patent and that said Letters Patent is hereby corrected as shown below:

On the Title Page

Item (71), in "Applicant", in Column 1, Line 1, delete "Elektra" and insert --Elekta-- therefor In the Claims In Column 26, Line 22, in Claim 6, delete "They" and insert --The-- therefor In Column 27, Line 46, in Claim 22, delete "They" and insert --The-- therefor In Column 28, Line 54, in Claim 34, delete "They" and insert --The-- therefor Signed and Sealed this
Eleventh Day of June, 2019

Andrei Iancu
*Director of the United States Patent and Trademark Office*